US012569602B2

(12) United States Patent
Ekdahl et al.

(10) Patent No.: US 12,569,602 B2
(45) Date of Patent: Mar. 10, 2026

(54) DIALYSIS SYSTEM AND METHOD INCLUDING A FLOW PATH INSULATOR

(71) Applicant: GAMBRO LUNDIA AB, Lund (SE)

(72) Inventors: Olof Ekdahl, Ljungbyhed (SE);
Carl-Henry Örndal, Eslöv (SE); **Olof
Jansson, Vellinge (SE); Henrik
Lindgren, Genarp (SE); Mats Nilsson**,
Veberöd (SE); Lars-Olof Nilsson,
Lomma (SE)

(73) Assignee: GAMBRO LUNDIA AB, Lund (SE)

( * ) Notice: Subject to any disclaimer, the term of this
patent is extended or adjusted under 35
U.S.C. 154(b) by 441 days.

(21) Appl. No.: 18/018,944

(22) PCT Filed: Jun. 23, 2021

(86) PCT No.: PCT/EP2021/067055
§ 371 (c)(1),
(2) Date: Jan. 31, 2023

(87) PCT Pub. No.: WO2022/022894
PCT Pub. Date: Feb. 3, 2022

(65) Prior Publication Data
US 2023/0277738 A1      Sep. 7, 2023

Related U.S. Application Data

(60) Provisional application No. 63/059,316, filed on Jul.
31, 2020.

(51) Int. Cl.
*A61M 1/28*          (2006.01)
*A61M 1/14*          (2006.01)
*A61M 1/36*          (2006.01)

(52) U.S. Cl.
CPC ............ *A61M 1/28* (2013.01); *A61M 1/1524*
(2022.05); *A61M 1/155* (2022.05);
(Continued)

(58) Field of Classification Search
CPC .... A61M 1/1524; A61M 1/153; A61M 1/155;
A61M 1/1561; A61M 1/1565;
(Continued)

(56) References Cited

U.S. PATENT DOCUMENTS

2018/0280604 A1    10/2018  Hobro et al.
2019/0275226 A1     9/2019  Burbank et al.
(Continued)

FOREIGN PATENT DOCUMENTS

EP          2616117 B1     12/2015

OTHER PUBLICATIONS

International Search Report from corresponding International Pat-
ent Application No. PCT/EP2021/067055, mailed Oct. 4, 2021.
(Continued)

*Primary Examiner* — John Kim
(74) *Attorney, Agent, or Firm* — K&L Gates LLP

(57)          ABSTRACT

A peritoneal dialysis system includes a cycler, a disposable
set operable with the cycler and including a patient line and
a drain line, one of (i) a water purifier for supplying purified
water for mixing to form fresh dialysis fluid at the disposable
set, (ii) at least one fresh dialysis fluid container provided as
part of the disposable set for supplying fresh dialysis fluid,
or (iii) a dialysis fluid preparation unit configured to supply
fresh dialysis fluid to the disposable set, and at least one flow
path insulator provided at the cycler, the water purifier, the
dialysis fluid preparation unit, and/or along the drain line.
The flow path insulator is configured to separate used
dialysis fluid flowing along the drain line into flow segments
to limit any current flowing from the patient to a drain.

31 Claims, 9 Drawing Sheets

(52) U.S. Cl.
CPC .......... *A61M 1/1561* (2022.05); *A61M 1/159*
(2022.05); *A61M 1/282* (2014.02); *A61M*
*1/284* (2014.02); *A61M 1/287* (2013.01);
*A61M 1/3624* (2013.01); *A61M 1/153*
(2022.05); *A61M 1/1565* (2022.05); *A61M*
*2205/12* (2013.01)

(58) Field of Classification Search
CPC ........ A61M 1/159; A61M 1/28; A61M 1/282;
A61M 1/284; A61M 1/287; A61M
1/3624; A61M 2205/12
See application file for complete search history.

(56) References Cited

U.S. PATENT DOCUMENTS

| | | |
|---|---|---|
| 2020/0122087 A1 | 4/2020 | Jansson et al. |
| 2020/0230301 A1 | 7/2020 | Beisser et al. |

OTHER PUBLICATIONS

Written Opinion from corresponding International Patent Application No. PCT/EP2021/067055, mailed Oct. 4, 2021.

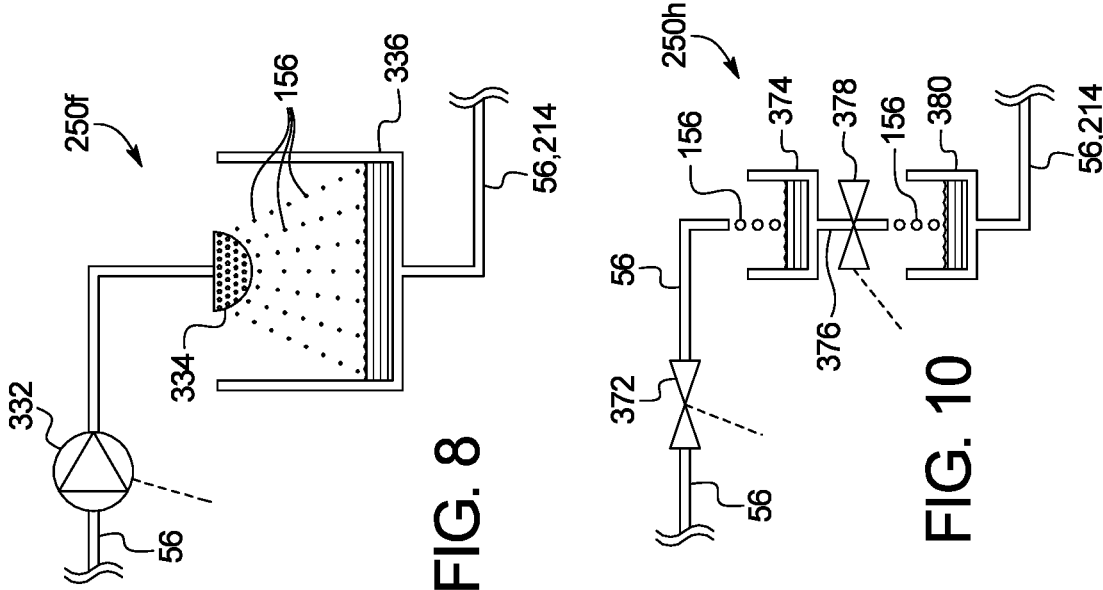
FIG. 8
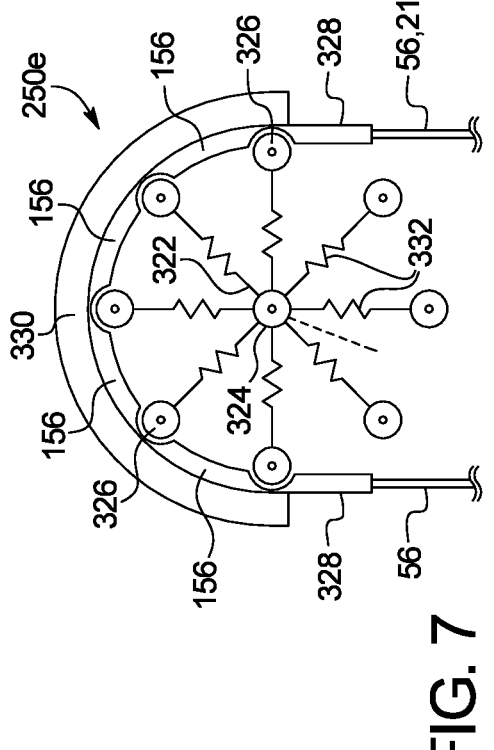
FIG. 7
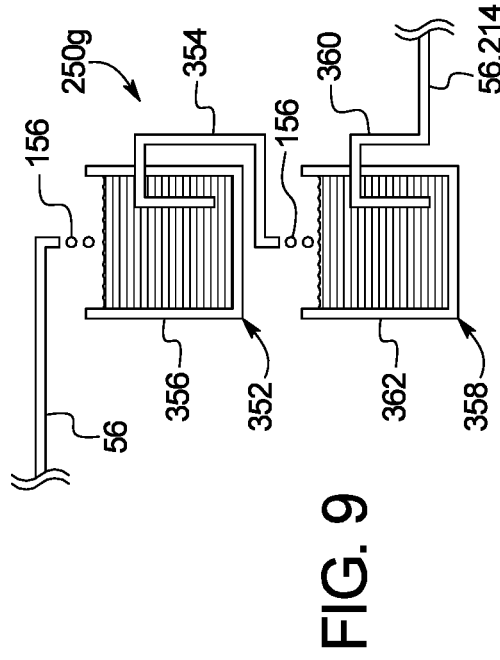
FIG. 10
FIG. 9

DIALYSIS SYSTEM AND METHOD INCLUDING A FLOW PATH INSULATOR

PRIORITY CLAIM

This application is a national phase entry of PCT/EP2021/067055, filed Jun. 23, 2021, which claims priority to U.S. Provisional Patent Application No. 63/059,316, filed Jul. 31, 2020, the entire disclosures of which are incorporated herein by reference.

BACKGROUND

The present disclosure relates generally to medical devices. More specifically, the present disclosure relates to the electrical insulation of medical devices.

Due to various causes, a person's renal system can fail. Renal failure produces several physiological derangements. It is no longer possible to balance water and minerals or to excrete daily metabolic load. Toxic end products of metabolism, such as, urea, creatinine, uric acid and others, may accumulate in a patient's blood and tissue.

Reduced kidney function and, above all, kidney failure is treated with dialysis. Dialysis removes waste, toxins and excess water from the body that normal functioning kidneys would otherwise remove. Dialysis treatment for replacement of kidney function is critical to many people because the treatment is lifesaving.

One type of kidney failure therapy is hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment. The substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Another type of kidney failure therapy is peritoneal dialysis ("PD"), which infuses a dialysis solution, also called dialysis fluid, into a patient's peritoneal cavity via a catheter. The dialysis fluid contacts the peritoneal membrane of the peritoneal cavity. Waste, toxins and excess water pass from the patient's bloodstream, through the peritoneal membrane, and into the dialysis fluid due to diffusion and osmosis, i.e., an osmotic gradient occurs across the membrane. An osmotic agent in the PD dialysis fluid provides the osmotic gradient. Used or spent dialysis fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), tidal flow dialysis and continuous flow peritoneal dialysis ("CFPD"). CAPD is a manual dialysis treatment. Here, the patient manually connects an implanted catheter to a drain to allow used or spent dialysis fluid to drain from the peritoneal cavity. The patient then switches fluid communication so that the patient catheter communicates with a bag of fresh dialysis fluid to infuse the fresh dialysis fluid through the catheter and into the patient. The patient disconnects the catheter from the fresh dialysis fluid bag and allows the dialysis fluid to dwell within the peritoneal cavity, wherein the transfer of waste, toxins and excess water takes place. After a dwell period, the patient repeats the manual dialysis procedure, for example, four times per day. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal cavity. APD machines also allow for the dialysis fluid to dwell within the cavity and for the transfer of waste, toxins and excess water to take place. The source may include multiple sterile dialysis fluid solution bags.

APD machines pump used or spent dialysate from the peritoneal cavity, though the catheter, and to the drain. As with the manual process, several drain, fill and dwell cycles occur during dialysis. A "last fill" may occur at the end of the APD treatment. The fluid may remain in the peritoneal cavity of the patient until the start of the next treatment, or may be manually emptied at some point during the day.

Medical devices are designated into different electrical categories. Cardiac Floating "CF" machines, for example, are machines having components ("applied parts"), which come into direct conductive contact with the patient's heart. Examples of CF machines are heart lung machines, external pacemakers, electrical surgery devices, pacemakers, and defibrillators. Body Floating "BF" machines have applied parts that come into conductive contact with the patient, or have medium or long term contact with the patient. Examples of BF machines include monitors, incubators and ultrasound equipment. Body ("B") machines have applied parts that are normally not conductive and may be immediately released from the patient. Examples of B machines include light emitting diode ("LED") lighting, medical lasers, MRI body scanners, hospital beds and photography equipment. CF and BF applied parts have floating patient grounds, while B machines may be connected to earth ground.

APD machines operate with a patient line that extends to the patient's peritoneal cavity and a drain line that in many instances extends to a house drain, such as a toilet, bathtub or sink. The toilet, bathtub or sink establishes an earth ground relative to the patient and the APD machine. During a drain phase of an APD treatment involving a house drain, the APD machine pumps used dialysis fluid from the patient's peritoneal cavity to the house drain and associated earth ground. Dialysis fluid, and thus used dialysis fluid, is conductive. The drain path accordingly creates a potential conductive path from the patient to the house drain. The primary resistance to the conductive path may only involve the fluid pumping mechanism, e.g., a pneumatically actuated membrane pump, for which a leaky fluid valve invites an uninterrupted electrical current path from the patient to earth ground.

A need accordingly exists to provide a mechanism and associated methodology for preventing an uninterrupted electrical current path from the patient to earth ground during a peritoneal dialysis treatment.

SUMMARY

The present disclosure provides a peritoneal dialysis ("PD") system and method that provides a flow path insulator that may be located along or operate with a drain line of a disposable set that operates with a cycler of the PD system. The flow path insulator creates a floating patient ground to protect the patient during treatment. There may be one or more portion of the drain line operating with the flow path insulator, such as a portion of the drain line extending along the cycler, a portion of the drain line located downstream of the cycler, a portion of the drain line extended to a water purifier and/or a portion of the drain line extended to a dialysis fluid preparation unit.

Discussed in detail herein are various ways to obtain and maintain flow path segments or discontinuous, separated used dialysis fluid flow. Alternatively or additionally, the resistance to an electrical current within the used dialysis fluid flow is increased to an extent that reduces any leakage current to a safe level.

In a first embodiment, any portion of which may be combined with any other flow path insulator embodiment described herein, a peritoneal dialysis system provides a flow path insulator including a first pump positioned and arranged to pump used dialysis fluid through the drain line to a first chamber and a second pump positioned and arranged to pump used dialysis fluid from an outlet of the first chamber to a second chamber. The separation of the first and second chambers creates the flow segments. The first and second pumps may be of the same or different type as the primary pumps of the cycler, and may for example be peristaltic or gear pumps operating with the drain line.

In various implementations of the first embodiment, the first pump is provided at the cycler, while the second or additional pumps is/are provided at or by (i) the water purifier, (ii) the dialysis fluid preparation unit, or (iii) along the drain line. The first and second pumps may alternatively both be provided at the cycler, the water purifier or the dialysis fluid preparation unit. In various implementations of the first embodiment, the first and second chambers are each provided at any of (i) the cycler, (ii) the water purifier, (iii) the dialysis fluid preparation unit, or (iv) along the drain line.

In one implementation, the flow path insulator of the first embodiment cycles between two states. In one state, no effluent flow exists between the first and second chambers. In a second state, no effluent flow exists between the first pump and the first chamber. An air gap exists accordingly at all times due to the no flow conditions of the first and second states.

In a second embodiment, any portion of which may be combined with any other flow path insulator embodiment described herein, a peritoneal dialysis system provides a flow path insulator including a first valve operable with a first fluid line and a second valve operable with a second fluid line, the first and second fluid lines leading to a chamber, the system configured to sequence the first and second valves to create the flow segments. In one implementation, the second flow path insulator further includes a pump positioned and arranged to pump used dialysis fluid from an outlet of the first chamber to an additional second chamber. The valves and pump may be (i) of the same or different type as the valves and pumps of the cycler, wherein the pump may, for example, be a peristaltic or gear pump operating with the drain line and (ii) located at one or more of the cycler, the water purifier or the dialysis fluid preparation unit. The addition of the second chamber and pump allow for a state to exist in which no effluent flow exists between the first and second chambers, which is provided in addition to the separation of fluid due to the sequencing of the two valves feeding the first chamber.

In a third embodiment, any portion of which may be combined with any other flow path insulator embodiment described herein, a peritoneal dialysis system provides a flow path insulator including a first pump positioned and arranged to pump used dialysis fluid through the drain line and a second pump positioned and arranged to introduce air or water into the drain line to create the flow segments. In the instance in which the intervening media is water, the water is deionized to provide non-conductive gaps between the conductive segments of used dialysis fluid. The deionized water may be provided by the water purifier or from a separate deionized water source.

In various implementations of the third embodiment, the first pump is provided at the cycler, e.g., is one of the primary pumps of the cycler, while the second pump is provided at or by (i) the water purifier, (ii) the dialysis fluid preparation unit, or (iii) along the drain line. The second pump may be of the same or different type as the first pump. The first and second pumps may alternatively both be provided at the cycler, the water purifier or the dialysis fluid preparation unit.

In a fourth embodiment, any portion of which may be combined with any other flow path insulator embodiment described herein, a peritoneal dialysis system provides a flow path insulator including a coiled length of tubing configured to create a high resistance to any electrical leakage current generated in the drain line. The coiled length may or may not naturally create flow segments or pockets. The coiled length of tubing may be disposable and located downstream from the cycler or reusable and located, e.g., inside the water purifier or the dialysis preparation unit. In one example, a ratio of a length (L) of the coiled length of tubing (310) to a cross-sectional area (A) of the coiled length of tubing is 10,000:8.

In a fifth embodiment, any portion of which may be combined with any other flow path insulator embodiment described herein, a peritoneal dialysis system provides a flow path insulator including a peristaltic pump configured to create the flow segments. The rotor and rollers of the pump may be configured to create a more pulsatile, segmented flow than normal. The peristaltic pump may be located in the cycler, in the water purifier, in the dialysis fluid preparation unit, or along the drain line. The peristaltic pump may also be the primary treatment pump of the PD cycler.

In a sixth embodiment, any portion of which may be combined with any other flow path insulator embodiment described herein, a peritoneal dialysis system provides a flow path insulator including an aspirator configured to create the flow segments or aspirated water droplets and a chamber configured to collect the flow segments or droplets from the aspirator. The aspirator may be provided in the form of a nozzle having multiple openings that create a spray or mist of water droplets or flow segments. The aspirator may be located in the cycler, in the water purifier, in the dialysis fluid preparation unit, or along the drain line.

In a seventh embodiment, any portion of which may be combined with any other flow path insulator embodiment described herein, a peritoneal dialysis system provides a flow path insulator including first and second siphons positioned and arranged to create a discontinuous drain flow to the house drain, e.g., toilet, bathtub or sink. Each siphon includes a siphon tube and a siphon chamber. The tube of the first siphon outputs to the chamber of the second siphon. The siphons act as flow switches that cycle between not having enough head pressure to push effluent out of the siphon and having enough head pressure to create effluent flow. The siphons may be provided in the water purifier, dialysis fluid preparation device or along the drain line.

In one implementation, the first and second siphons operate in first and second states. In a first state, effluent flows from the cycler to the chamber of the first siphon, wherein the first siphon chamber fills, building head pressure, while the second siphon chamber drains, losing head pressure. Here, an effluent air gap exists between the first and second siphon chambers. In a second state, effluent still flows from the cycler to the chamber of the first siphon, but here the first siphon chamber drains, losing head pressure, while the second siphon fills, gaining head pressure. Here, an effluent gap exists between the second siphon chamber and the house drain. To create the first and second states in one embodiment, (i) the first siphon is configured to drain at a flowrate greater than the drain flowrate from the cycler to the first siphon, and (ii) the first and second siphons are configured such that their switch states between building vs. losing head pressure for the first siphon and losing vs. building head pressure for the second siphon, and vice versa, occur at the same time or substantially the same time.

In an eighth embodiment, any portion of which may be combined with any other flow path insulator embodiment described herein, a peritoneal dialysis system provides a flow path insulator having a first chamber including an output directed towards, but separate from, a second chamber to create the flow segments. A valve may be located in either or both of the lines outputting to the first and second chambers. In various implementations of the eighth embodiment, the first chamber is provided at the cycler, while the second chamber is provided at or by (i) the water purifier, (ii) the dialysis fluid preparation unit, or (iii) along the drain line. In other implementations, both chambers are provided at or by the cycler, the water purifier, the dialysis fluid preparation unit, or along the drain line.

In a ninth embodiment, any portion of which may be combined with any other flow path insulator embodiment described herein, the flow path insulator includes a chamber that receives used dialysis fluid. The chamber is hinged via a hinge and is configured to tip via the weight of used dialysis fluid entering the chamber. When the chamber tips, the chamber fills a siphon enough such that head pressure within the siphon causes used dialysis fluid to flow from the siphon to a house drain. The chamber may be provided with a counterweight that returns the chamber to its original position after delivering the dialysis fluid. Alternatively, a biasing device (e.g., a spring) may be positioned and arranged to return the chamber to a filling position after tipping. An electrical switch that switches from a first state to a second state when the first chamber is tipped may also be provided to prevent the flow of used dialysis fluid from the cycler to the chamber until the chamber is righted to its upright position and the switch is returned to its first state.

In a tenth embodiment, any portion of which may be combined with any other flow path insulator embodiment described herein, the flow path insulator includes a container located upstream from a first chamber, wherein the first chamber is located upstream from a first pump, wherein the first pump is located upstream from a second chamber, and wherein the second chamber is located upstream from a second pump. The first and second pumps are sequenced to separate used dialysis fluid flowing along the drain line to limit current flowing from the patient to the house drain. In one implementation, used dialysis fluid flow from the first chamber to the second chamber is prevented when used dialysis fluid flows from the second chamber to a house drain to create separated effluent flow.

In an eleventh embodiment, any portion of which may be combined with any other flow path insulator embodiment described herein, the flow path insulator is provided at or by at least one of the cycler, the water purifier, the dialysis fluid preparation unit, or along the drain line. The flow path insulator is here configured to separate used dialysis fluid flowing along the drain line by pumping used dialysis fluid to a drain container during a drain phase and pumping used dialysis from the drain container to a house drain during a fill and/or dwell phase to limit current flowing from the patient to the house drain. In one implementation, the flow path insulator of the eleventh embodiment includes a chamber in fluid communication with the drain container, wherein the chamber creates an air gap in the used dialysis fluid. A pump may be located downstream from the drain container, which is actuated during a fill and/or dwell phase to pull effluent from the drain container to a house drain.

In a twelfth embodiment, any portion of which may be combined with any other flow path insulator embodiment described herein, the flow path insulator includes a first chamber, a second chamber and a pump located downstream from the first and second chambers. First and second inlet valves are placed in fluid communication with the first and second chambers, respectively. First and second outlet valves are placed in fluid communication with the first and second chambers, respectively. The first and second inlet and outlet valves are sequenced such that used dialysis fluid flow into one of the first or second chambers occurs while used dialysis fluid is removed from the other of the first or second chambers to separate used dialysis fluid flowing along the drain line to limit current flowing from the patient to the house drain. In one implementation, (i) in a first state the first inlet valve and the second outlet valve are open while the second inlet valve and the first outlet valve are closed and (ii) in a second state the second inlet valve and the first outlet valve are open while the first inlet valve and the second outlet valve are closed. Used dialysis fluid is delivered to the first and second chambers via a primary pump of the cycler in one implementation.

In a thirteenth embodiment, any portion of which may be combined with any other flow path insulator embodiment described herein, the flow path insulator includes a pivoting device or cradle, which pivots back and forth under the weight of incoming used dialysis fluid or effluent to create flow segments. Used dialysis fluid flows continuously along a drain line and into a container having the pivoting device or cradle at the top of the container, wherein the pivoting is structured such that used dialysis fluid falling into the cradle impinges or contacts one side or other of a middle wall separating the cradle into two compartments. The side of the wall that is currently being contacted belongs to the compartment that is filling, such that the compartment is isolated from earth ground at the end of the drain line. The side of the wall that is not currently being contacted belongs to the other compartment, which is draining into the container, which in turn drains to the distal end of the drain line and to house drain, such that this other compartment is isolated from the patient.

The flow path insulator of the thirteenth embodiment may be located at the cycler, at a water purifier or dialysis fluid preparation unit operating with the cycler, or anywhere along the drain line.

It is contemplated that when any of the flow path insulator embodiments described herein having a chamber into which used dialysis fluid flows to a chamber is provided as part of a water purifier or dialysis fluid preparation unit, that the chamber also receive at least one additional incoming fluid stream, e.g., a water purification device reject stream. The water purification device may for example be a reverse osmosis unit, an ultrafilter or any other purification device having a reject output. Such configuration uses a single chamber for multiple purposes. The at least one additional incoming fluid stream may or may not be provided with its own flow path insulation.

In light of the technical features set forth herein, and without limitation, in a first aspect, which may be combined with any other aspect described herein (or portion thereof), a peritoneal dialysis system includes: a cycler; a disposable set including a patient line and a drain line, the cycler configured to pump fresh dialysis fluid to a patient via the patient line and used dialysis fluid from the patient via the drain line; one of (i) a water purifier for supplying purified water for mixing to form fresh dialysis fluid at the disposable set, (ii) at least one fresh dialysis fluid container provided as part of the disposable set for supplying fresh dialysis fluid, or (iii) a dialysis fluid preparation unit configured to supply fresh dialysis fluid to the disposable set; and at least one flow path insulator provided at or by at least one of the cycler, the water purifier, the dialysis fluid preparation unit, or along the drain line, the flow path insulator configured to separate used dialysis fluid flowing along the drain line to limit current flowing from the patient to a house drain.

In a second aspect, which may be combined with any other aspect described herein (or portion thereof), the drain line extends to the water purifier so that at least a portion of the flow path insulator provided at or by the water purifier can separate used dialysis fluid flowing along the drain line.

In a third aspect, which may be combined with any other aspect described herein (or portion thereof), the drain line extends to the dialysis preparation unit so that at least a portion of the flow path insulator provided at or by the dialysis fluid preparation unit can separate used dialysis fluid flowing along the drain line.

In a fourth aspect, which may be combined with any other aspect described herein (or portion thereof), the drain line extends along the cycler so that at least a portion of the flow path insulator located at or by the cycler can separate used dialysis fluid flowing along the drain line.

In a fifth aspect, which may be combined with any other aspect described herein (or portion thereof), the flow path insulator includes a first pump positioned and arranged to pump used dialysis fluid through the drain line to a first chamber and a second pump positioned and arranged to pump used dialysis fluid from an outlet of the first chamber to a second chamber, the operation of the first and second pumps separating the used dialysis fluid to limit current flowing from the patient to the house drain.

In a sixth aspect, which may be combined with any other aspect described herein (or portion thereof), the first pump is provided at the cycler and the second pump is provided at or by the water purifier, the dialysis fluid preparation unit, or along the drain line.

In a seventh aspect, which may be combined with any other aspect described herein (or portion thereof), the first pump is a primary pump of the cycler.

In an eighth aspect, which may be combined with any other aspect described herein (or portion thereof), the first and second chambers are each provided at any of the cycler, the water purifier, the dialysis fluid preparation unit, or along the drain line.

In a ninth aspect, which may be combined with any other aspect described herein (or portion thereof), the flow path insulator includes a first valve operable with a first fluid line and a second valve operable with a second fluid line, the first and second fluid lines leading to chamber, the system configured to sequence the first and second valves to separate the used dialysis fluid to limit current flowing from the patient to the house drain.

In a tenth aspect, which may be combined with any other aspect described herein (or portion thereof), the flow path insulator further includes a pump positioned and arranged to pump used dialysis fluid from an outlet of the chamber to a second chamber, the system configured to sequence the first and second valves and the operation of the pump to separate the used dialysis fluid to limit current flowing from the patient to the house drain.

In an eleventh aspect, which may be combined with any other aspect described herein (or portion thereof), the flow path insulator includes a first pump positioned and arranged to pump used dialysis fluid through the drain line and a second pump positioned and arranged to introduce air or water into the drain line to create used dialysis fluid flow separating segments to limit current flowing from the patient to the house drain.

In a twelfth aspect, which may be combined with any other aspect described herein (or portion thereof), the first pump is provided at the cycler and the second pump is provided at or by the water purifier, the dialysis fluid preparation unit, or along the drain line.

In a thirteenth second aspect, which may be combined with any other aspect described herein, any of the pumps are peristaltic or gear pumps.

In a fourteenth aspect, which may be combined with any other aspect described herein (or portion thereof), the flow path insulator includes a chamber that receives used dialysis fluid, the chamber hinged via a hinge and configured to tip via weight of the used dialysis fluid so that the used dialysis fills a siphon enough such that head pressure within the siphon causes used dialysis fluid to flow from the siphon.

In a fifteenth aspect, which may be combined with any other aspect described herein (or portion thereof), the flow path insulator includes at least one of (i) a biasing device positioned and arranged to return the chamber to a filling position after tipping or (ii) a switch that switches from a first state to a second state when the first chamber is tipped to prevent flow of used dialysis fluid to the chamber until the switch is returned to the first state.

In a sixteenth aspect, which may be combined with any other aspect described herein (or portion thereof), the flow path insulator includes a peristaltic pump configured to create flow separating segments to limit current flowing from the patient to the house drain.

In a seventeenth aspect, which may be combined with any other aspect described herein (or portion thereof), the flow path insulator includes an aspirator configured to create flow separating segments to limit current flowing from the patient to the house drain, and a chamber configured to collect the flow separating segments from the aspirator.

In an eighteenth aspect, which may be combined with any other aspect described herein (or portion thereof), the flow path insulator includes a first siphon and a second siphon, wherein the system is configured to prevent the first siphon from creating enough head pressure for used dialysis fluid flow from the first siphon to the second siphon until head pressure in the second siphon falls such that used dialysis fluid does not flow from the second siphon, separating used dialysis fluid flowing along the drain line to limit current flowing from the patient to the house drain.

In a nineteenth aspect, which may be combined with any other aspect described herein (or portion thereof), the first siphon includes a first siphon tube and a first siphon chamber and the second siphon includes a second siphon tube and a second siphon chamber.

In a twentieth, which may be combined with any other aspect described herein (or portion thereof), the flow path insulator includes a first chamber having an output directed towards but separate from a second chamber, a first valve upstream from the first chamber and a second valve upstream of the second chamber, the first and second valves sequenced to separate used dialysis fluid flowing along the drain line to limit current flowing from the patient to the house drain.

In a twenty-first aspect, which may be combined with any other aspect described herein (or portion thereof), the first and second valves are sequenced such that used dialysis fluid flow to the first chamber is prevented if the second valve is open and the second valve is opened when the second chamber is empty.

In a twenty-second aspect, which may be combined with any other aspect described herein (or portion thereof), the flow path insulator includes a container located upstream from a first chamber, the first chamber located upstream from a first pump, the first pump located upstream from a second chamber, the second chamber located upstream from a second pump, the first and second pumps sequenced to separate used dialysis fluid flowing along the drain line to limit current flowing from the patient to the house drain.

In a twenty-third aspect, which may be combined with any other aspect described herein (or portion thereof), used dialysis fluid flow from the first chamber to the second chamber is prevented when used dialysis fluid flows from the second chamber.

In a twenty-fourth aspect, which may be combined with any other aspect described herein (or portion thereof), the flow path insulator includes a first chamber, a second chamber and a pump downstream from the first and second chambers, first and second inlet valves in fluid communication with the first and second chambers, respectively, first and second outlet valves in fluid communication with the first and second chambers, respectively, the first and second inlet and outlet valves sequenced such that used dialysis fluid flow into one of the first and second chambers occurs while used dialysis fluid is removed from the other of the first and second chambers, separating used dialysis fluid flowing along the drain line to limit current flowing from the patient to the house drain.

In a twenty-fifth aspect, which may be combined with any other aspect described herein (or portion thereof), (i) in a first state the first inlet valve and the second outlet valve are open while the second inlet valve and the first outlet valve are closed and (ii) in a second state the second inlet valve and the first outlet valve are open while the first inlet valve and the second outlet valve are closed.

In a twenty-sixth aspect, which may be combined with any other aspect described herein (or portion thereof), used dialysis fluid is delivered to the first and second chambers via a primary pump of the cycler.

In a twenty-seventh aspect, which may be combined with any other aspect described herein (or portion thereof), the flow path insulator includes a pivoting device that pivots about a pivot, the pivoting device including first and second compartments that alternatingly fill and drain used dialysis fluid, separating the used dialysis fluid flowing along the drain line to limit current flowing from the patient to the house drain.

In a twenty-eighth aspect, which may be combined with any other aspect described herein (or portion thereof), the at least one flow path insulator is provided at or by the water purifier or the dialysis fluid preparation unit, and which includes at least one water purification device having a reject line outputting to the flow path insulator.

In a twenty-ninth aspect, which may be combined with any other aspect described herein (or portion thereof), the peritoneal dialysis system includes at least one valve provided along the at least one respective reject line, the at least one valve sequenced open and closed to create flow path segments.

In a thirtieth first aspect, which may be combined with any other aspect described herein (or portion thereof), the at least one flow path insulator includes a valve sequenced open and closed to create flow path segments.

In a thirty-first aspect, which may be combined with any other aspect described herein (or portion thereof), a perito-neal dialysis system (10) includes a cycler; a disposable set including a patient line and a drain line, the cycler config-ured to pump fresh dialysis fluid to a patient via the patient line and used dialysis fluid from the patient via the drain line; one of (i) a water purifier for supplying purified water for mixing to form fresh dialysis fluid at the disposable set, (ii) at least one fresh dialysis fluid container provided as part of the disposable set for supplying fresh dialysis fluid, or (iii) a dialysis fluid preparation unit configured to supply fresh dialysis fluid to the disposable set; and at least one flow path insulator provided at or by at least one of the cycler, the water purifier, the dialysis fluid preparation unit, or along the drain line, the flow path insulator configured to separate used dialysis fluid flowing along the drain line by pumping used dialysis fluid to a drain container during a drain phase and pumping used dialysis from the drain container to a house drain during a fill and/or dwell phase to limit current flowing from the patient to the house drain.

In a thirty-second aspect, which may be combined with any other aspect described herein (or portion thereof), the flow path insulator includes a chamber in fluid communi-cation with the drain container, the chamber creating an air gap in the used dialysis fluid.

In a thirty-third aspect, which may be combined with any other aspect described herein (or portion thereof), the flow path insulator includes a pump located downstream from the drain container, the pump actuated during the fill and/or dwell phase.

In a thirty-fourth aspect, which may be combined with any other aspect described herein (or portion thereof), a peritoneal dialysis system includes a cycler; a disposable set including a patient line and a drain line, the cycler config-ured to pump fresh dialysis fluid to a patient via the patient line and used dialysis fluid from the patient via the drain line; one of (i) a water purifier for supplying purified water for mixing to form fresh dialysis fluid at the disposable set, (ii) at least one fresh dialysis fluid container provided as part of the disposable set for supplying fresh dialysis fluid, or (iii) a dialysis fluid preparation unit configured to supply fresh dialysis fluid to the disposable set; and at least one flow path insulator provided at or by at least one of the cycler, the water purifier, the dialysis fluid preparation unit, or along the drain line, wherein the flow path insulator includes a coiled length of tubing sized to increase a resistance to a leakage current residing in used dialysis fluid flowing through the coiled length of tubing.

In a thirty-fifth aspect, which may be combined with any other aspect described herein (or portion thereof), a ratio of a length (L) of the coiled length of tubing (310) to a cross-sectional area (A) of the coiled length of tubing is 10,000:8.

In a thirty-sixth aspect, which may be combined with any other aspect described herein (or portion thereof), the patient line is also used as a portion of the drain line.

In a thirty-seventh aspect, which may be combined with any other aspect described herein (or portion thereof), wherein any of the pumps or valves are operated under the control of at least one control unit.

In a thirty-eighth aspect, which may be combined with any other aspect described herein (or portion thereof), wherein the at least one control unit is a control unit of the cycler, the water purifier or the dialysis fluid preparation device.

In a thirty-ninth aspect, which may be combined with any other aspect described herein (or portion thereof), the control unit includes one or more processor and one or more memory.

In a fortieth aspect, which may be combined with any other aspect described herein (or portion thereof), wherein the control unit of the cycler is in wired or wireless communication with the control unit of the water purifier or the dialysis fluid preparation device.

In an additional aspect of the present disclosure, any of the features, functionality and alternatives described in connection with any one or more of FIGS. 1 to 16 may be combined with any of the features, functionality and alternatives described in connection with any of the other one or more of FIGS. 1 to 16.

It is therefore an advantage of the present disclosure to provide a peritoneal dialysis ("PD") system and method having electrical isolation.

It is another advantage of the present disclosure to provide a PD system and method that actively prevents or reduces electrical currents resulting from voltages due to fault conditions by creating flow segments and/or by increasing a resistance to the electrical current.

It is a further advantage of the present disclosure to provide a PD system and method that actively prevents or reduces electrical currents resulting from voltages due to fault conditions, and which is relatively easy and cost effective to implement.

It is yet another advantage of the present disclosure to provide a PD system and method having electrical isolation that is adaptable to different types of PD fluid supplies, including bagged, online mixing at the cycler and online mixing upstream of the cycler.

Moreover, it is an advantage of the present disclosure to provide a PD system and method having electrical isolation that may be separated and located at different parts of the system.

In certain embodiments, it is advantageous to make use of the different cycles of a peritoneal dialysis treatment to create flow isolation. Here, for example, used dialysis fluid may be separated by pumping the fluid to a drain container during a drain phase, and pumping the used dialysis fluid from the drain container to a house drain during a fill and/or dwell phase. In doing so, the patient is always isolated from earth ground located at the end of the drain line.

In certain embodiments, it is advantageous to use already existing equipment to implement the flow path insulation.

For example, the cycler pump that pumps fresh dialysis fluid to the patient and removed used dialysis fluid from the patient may be used additionally as the only pump or as one of multiple pumps for operating a flow path insulator of the present disclosure. In another example, a water purifier pump that pumps water for purification may be used additionally as the only pump or as one of multiple pumps for operating a flow path insulator of the present disclosure. In a further example, a dialysis fluid preparation unit pump that pumps water or online generated dialysis fluid for treatment may be used additionally as the only pump or as one of multiple pumps for operating a flow path insulator of the present disclosure.

Additional features, technical effects and advantages are described in, and will be apparent from, the following Detailed Description and the DRAWINGS. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

BRIEF DESCRIPTION OF THE FIGURES

FIG. 7 is a side elevation view of a fifth embodiment for a flow path insulator of the present disclosure.

FIG. 8 is a side elevation view of a sixth embodiment for a flow path insulator of the present disclosure.

FIG. 9 is a side elevation view of a seventh embodiment for a flow path insulator of the present disclosure.

FIG. 10 is a side elevation view of an eighth embodiment for a flow path insulator of the present disclosure.

DETAILED DESCRIPTION

System Overview

The examples described herein are applicable to any medical fluid therapy system that delivers a medical fluid that may be bagged or mixed at the point of use, prior to and/or during treatment, such as dialysis fluid, substitution fluid, or an intravenous drug. The examples are particularly well suited for kidney failure therapies, such as all forms of peritoneal dialysis ("PD"), hemodialysis ("HD"), hemofiltration ("HF"), hemodiafiltration ("HDF") and continuous renal replacement therapies ("CRRT"), referred to herein collectively or generally individually as renal failure therapy. Moreover, the machines described herein may be used in clinical or home settings. For example, the machines and associated methods may be employed in an in-center PD or HD machine, which runs virtually continuously throughout the day. Alternatively, the machine and methods may be used in a home PD or HD machine, which can for example be run at night while the patient is sleeping. The machines and methods discussed herein are also applicable to medical delivery applications. The following examples will be described in the setting of a peritoneal dialysis system having point of use dialysis fluid production but may instead be used to make point of use treatment fluid for any of the above modalities. Moreover, point of use dialysis fluid production is not required for the present disclosure and the dialysis fluid may be provided instead premade in containers or bags.

Figure 1:
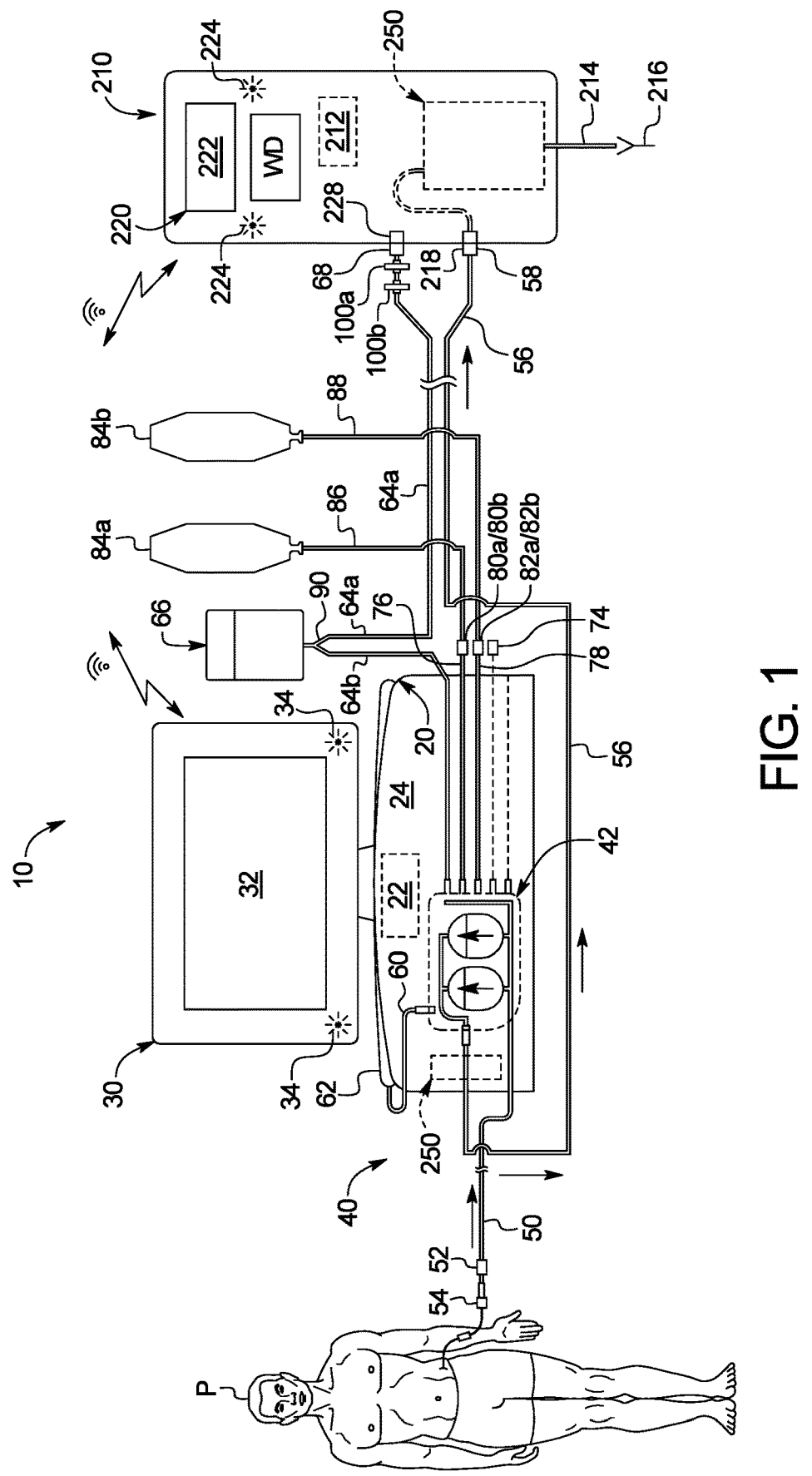
FIG. 1 is a front elevation view of one embodiment of a medical fluid delivery system having point of use dialysis fluid production and a flow path insulator of the present disclosure.

Referring now to the drawings and in particular to FIG. 1, one embodiment of a peritoneal dialysis system having point of use dialysis fluid production of the present disclosure is illustrated by system 10. System 10 includes a medical fluid delivery machine or cycler 20 and a water purifier 210. Suitable cyclers for cycler 20 include, e.g., the Amia®, HomeChoice® and Claria® cyclers marketed by Baxter International Inc., with the understanding that those cyclers may be provided with updated programming to perform and use the point of use dialysis fluid produced according to system 10. To this end, cycler 20 includes a control unit 22 having at least one processor and at least one memory. Control unit 22 further incudes a wired or wireless transceiver for sending information to and receiving information from a water purifier 210. Water purifier 210 also includes a control unit 212 having at least one processor and at least one memory. Control unit 212 further incudes a wired or wireless transceiver for sending information to and receiving information from control unit 22 of cycler 20. Wired communication may be via Ethernet connection, RS232, wired USB, for example. Wireless communication may be performed via any of Bluetooth™, WiFi™, Zigbee®, Z-Wave®, wireless Universal Serial Bus ("USB"), or infrared protocols, or via any other suitable wireless communication technology.

Cycler 20 includes a housing 24, which holds equipment programmed via control unit 22 to prepare fresh dialysis solution at the point of use, pump the freshly prepared dialysis fluid to patient P, allow the dialysis fluid to dwell within patient P, then pump used dialysis fluid to a drain. In the illustrated embodiment, water purifier 210 includes a drain line 214 leading to a drain 216, which for the flow path insulating examples described herein is a house drain, such as a toilet, bathtub or sink. The equipment programmed via control unit 22 to prepare fresh dialysis solution at the point of use in an embodiment includes equipment for a pneumatic pumping system, including but not limited to (i) positive and negative pressure reservoirs, (ii) a compressor and a vacuum pump or a single pump creating both positive and negative pressure, (iii) plural pneumatic valve chambers for delivering positive and negative pressure to plural fluid valve chambers, (iv) plural pneumatic pump chambers for delivering positive and negative pressure to plural fluid pump chambers, (v) plural electrically actuated on/off pneumatic solenoid valves, (vi) plural electrically actuated variable orifice pneumatic valves, (vii) a heater under control of control unit 22 for heating the dialysis fluid as it is being mixed in one embodiment, and (viii) an occluder for closing patient and drain lines in alarm and other situations.

In one embodiment, the plural pneumatic valve chambers and the plural pneumatic pump chambers are located on a front face or surface of housing 24 of cycler 20. The heater is located inside housing 24 and in an embodiment includes heating coils that contact a heating pan or tray, which is located at the top of housing 24, beneath a heating lid (not seen in FIG. 1).

Cycler 20 in the illustrated embodiment includes a user interface 30 under control of control unit 22, which in an embodiment includes a video controller for interfacing with a video monitor 32 of user interface. Video monitor may operate with a touch screen overlay placed onto video monitor 32 for inputting commands via user interface 30 into control unit 22. User interface 30 may also include one or more electromechanical input device, such as a membrane switch or other button. Control unit 22 may further include an audio controller for playing sound files, such as voice activation commands, at one or more speaker 34.

Water purifier 210 in the illustrated embodiment also includes a user interface 220. User interface 220 includes a video monitor 222, which may likewise operate with a touch screen overlay placed onto video monitor 222 for inputting commands into control unit 212. User interface 220 may also include one or more electromechanical input device, such as a membrane switch or other button. Control unit 212 may further include an audio controller for playing sound files, such as alarm or alert sounds, at one or more speaker 224 of water purifier 210.

Figure 2:
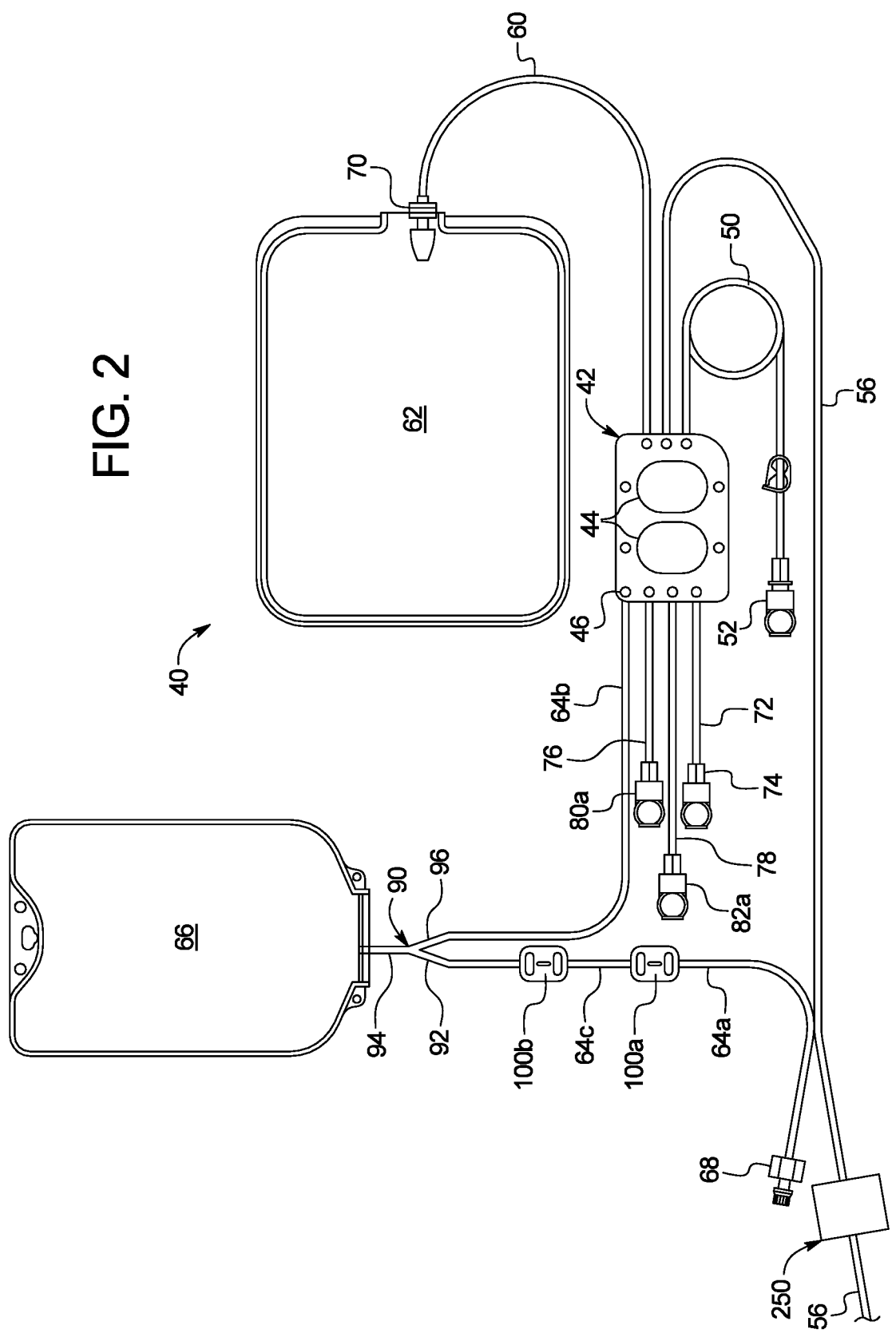
FIG. 2 is an elevation view of one embodiment of a disposable set used with the system illustrated in FIG. 1 and having a flow path insulator of the present disclosure.

Referring additionally to FIG. 2, one embodiment of disposable set 40 is illustrated. Disposable set 40 is also illustrated in FIG. 1, mated to cycler 20 to move fluid within the disposable set 40, e.g., to mix dialysis fluid as discussed herein. Disposable set 40 in the illustrated embodiment includes a disposable cassette 42, which may include a planar rigid plastic piece covered on one or both sides by a flexible sheet. One of the flexible sheets pressed against housing 24 of cycler 20 forms a pumping and valving membrane. FIG. 2 illustrates that disposable cassette 42 includes fluid pump chambers 44 that operate with the pneumatic pump chambers located at housing 24 of cycler 20 and fluid valve chambers 46 that operate with the pneumatic valve chambers located at housing 24 of cycler 20. Pump chambers 44 provide the primary pump or pumping mechanism for cycler 20.

FIGS. 1 and 2 illustrate that disposable set 40 includes a patient line 50 that extends from a patient line port of cassette 42 and terminates at a patient line connector 52. FIG. 1 illustrates that patient line connector 52 connects to a patient transfer set 54, which in turn connects to an indwelling catheter located in the peritoneal cavity of patient P. Disposable set 40 includes a drain line 56 that extends from a drain line port of cassette 42 and terminates at a drain line connector 58. FIG. 1 also illustrates that drain line 56 extends along a section of cycler 20, so that at least a portion of flow path insulator 250 (multiple versions of which are described below) may be located at cycler 20 and be operable with drain line 56. FIG. 1 also illustrates that drain line connector 58 connects removeably to a drain connector 218 of water purifier 210.

FIGS. 1 and 2 further illustrate that disposable set 40 includes a heater/mixing line 60 that extends from a heater/mixing line port of cassette 42 and terminates at a heater/mixing bag 62. Disposable set 40 includes an upstream water line segment 64a that extends to a water inlet leg 92 of a Y-connector 90 (or T-connector, or the like) located just upstream of water accumulator 66. Y-connector 90 connects to water accumulator 66 via leg 94. A downstream water line segment 64b extends from a water outlet leg 96 of Y-connector 90 to cassette 42. In the illustrated embodiment, upstream water line segment 64a begins at a water line connector 68 and is located upstream from water accumulator 66. FIG. 1 illustrates that water line connector 68 is removeably connected to a water outlet connector 228 of water purifier 210.

Water purifier 210 outputs water and possibly water suitable for peritoneal dialysis ("WFPD"). To ensure WFPD, however, a sterilizing grade filter 100a is placed upstream from a downstream sterilizing grade filter 100b, respectively. Water purifier 210 outputs deionized water in one embodiment, which is important in particular for one of the flow path insulators described below.

FIG. 2 further illustrates that a last bag or sample line 72 may be provided that extends from a last bag or sample port of cassette 42 and terminates at a connector 74, which may be connected to a mating connector of a premixed last fill bag of dialysis fluid or to a sample bag or other sample collecting container.

FIGS. 1 and 2 illustrate that disposable set 40 includes a first, e.g., glucose, concentrate line 76 that terminate at connector 80a. A second, e.g., buffer, concentrate line 78 terminates at a second, e.g., buffer, cassette concentrate connector 82a. A first concentrate container 84a holds a first, e.g., glucose, concentrate, which is pumped through a container line 86 to a first container concentrate connector 80b, which mates with first cassette concentrate connector 80a. A second concentrate container 84b holds a second, e.g., buffer, concentrate, which is pumped through a container line 88 to a second container concentrate connector 82b, which mates with second cassette concentrate connector 82a.

For disposable set 40, the rigid portion of cassette 42 may be made for example of a thermal olefin polymer of amorphous structure ("TOPAS") cyclic olefin copolymer ("coc"). The flexible membranes of cassette 42 may be made for example of a copolyletser ether ("PCCE") and may be of one or more layer. Any of the tubing or lines and Y-connector 90 may be made for example of polyvinyl chloride ("PVC"). Any of the connectors may be made for example of acrylonitrile-butadiene-styrene ("ABS", e.g., for Y-connector 90 (alternatively), for connector 70 of heater/mixing container or bag 62 and/or for concentrate connectors 80a, 80b, 82a, 82b discussed below), acrylic (e.g., for drain line connector 58) or PVC (e.g., for water line connector water line connector 68). Any of the bags or containers, such as heater/mixing container or bag 62 discussed below, may be made of PVC. The materials for any of the above components may be changed over time. Moreover, any of the materials discussed above may be used for any of the flow path insulators 250 described herein.

Control unit 22 may be programmed to cause cycler 20 to perform one or more mixing action to help mix dialysis fluid properly and homogeneously for treatment. Mixing is performed at pump chambers 44 of cassette 42 and/or in heater/mixing container or bag 62.

The flow path insulators 250 (referring to any one or more or all of insulators 250a to 250l) described in detail below may be located within water purifier 210, connected to drain connector 218 and separating disposable set drain line 56 from water purifier drain line 214 as illustrated in FIG. 1. The flow path insulators 250 (referring to at any one or more or all of insulators 250a to 250l) may be located alternatively within cycler 20 and be operable with drain line 56 as illustrated in FIG. 1. The flow path insulators 250 (referring to any one or more or all of insulators 250a to 250l) may be located further alternatively along, e.g., at the end of, drain line 56 of disposable set 40 as illustrated in FIG. 2. Further alternatively, different portions of flow path insulators 250 may be located at multiple ones of purifier 210, cycler 20 and/or drain line 56.

In an alternative embodiment, water purifier 210, first and second concentrate containers 84a and 84b and respective concentrate lines 86 and 88, and water accumulator 66 and water line segments 64a and 64b, including sterilizing grade filters 100a and 100b, are not provided. Instead, premade and presterilized fresh dialysis fluid containers or bags (not illustrated) are placed in fluid communication with the top three ports of disposable cassette 42 previously in fluid communication with containers 84a and 84b and water accumulator 66. In this alternative embodiment, flow path insulators 250 (referring collectively to any one or more or all of insulators 250a to 250l) described in detail below are located (i) within cycler 20 and operable with drain line 56 as illustrated in FIG. 1 or (ii) along, e.g., at the end of, drain line 56 of disposable set 40 as illustrated in FIG. 2. Further alternatively, different portions of insulators 250 may be located at cycler 20 and/or drain line 56.

In another alternative embodiment, water purifier 210, first and second concentrate containers 84a and 84b and respective concentrate lines 86 and 88, and water accumulator 66 and water line segments 64a and 64b, including sterilizing grade filters 100a and 100b, are not provided. Instead, a dialysis fluid preparation unit is provided that mixes purified water, e.g., WFPD, with one or more concentrate, e.g., PD concentrate, to produce fresh dialysis fluid, e.g., fresh PD fluid. Drain line 56 may extend from cycler 20 to the dialysis fluid preparation in a similar manner as illustrated in FIG. 1, wherein drain line 56 extends to water purifier 210. Here, flow path insulators 250 (referring to any one or more or all of insulators 250a to 250l) may be located (i) within the dialysis fluid preparation unit, connected to drain connector and separating disposable set drain line 56 from a dialysis fluid preparation unit drain line, (ii) within cycler 20 and operable with drain line 56 as illustrated in FIG. 1 or (iii) along, e.g., at the end of, drain line 56 of disposable set 40 as illustrated in FIG. 2. Further alternatively, different portions of flow path insulators 250 may be located at multiple ones of the dialysis fluid preparation device, cycler 20 and/or drain line 56.

It is also contemplated to provide a peritoneal dialysis machine (not illustrated), e.g., single enclosure, that performs each of (i) water purification, (ii) peritoneal dialysis fluid mixing using purified water and one or more concentrate, and (iii) treatment, delivering fresh peritoneal dialysis fluid to the patient, allowing the fluid to dwell within the patient, and removed used dialysis fluid and patient ultrafiltration from the patient when the dwell is completed.

Here, any one or more of flow path insulators 250a to 250l may be provided at the all-in-one machine, along drain line 56 leading from such machine, or have a portion provided at the all-in-one machine and a portion provided along the drain line.

Flow Path Insulators

Flow path insulators 250 illustrated herein may include one or more drain fluid collection area, e.g., a chamber. The collection areas or chambers may be reusable or disposable and may be made of any suitable metal or polymer. If metal, the collection areas or chambers may be stainless steel, steel or aluminum. If a polymer or plastic, the collection areas or chambers may be made of any of the polymers or plastics listed above. The tubing running to or between the collection areas or chambers may likewise be reusable or disposable and may be made of any suitable metal or polymer. If metal, the tubing may be stainless steel. If a polymer or plastic, the tubing may be made of any of the polymers or plastics listed above. It is also noted that in any one or more of FIGS. 3 to 14 below, the dashed lines leading from the components indicate that such components are under control of control unit 22 of cycler 20 or control unit 212 of water purifier 210.

Figures 3, 4, 5, 6:
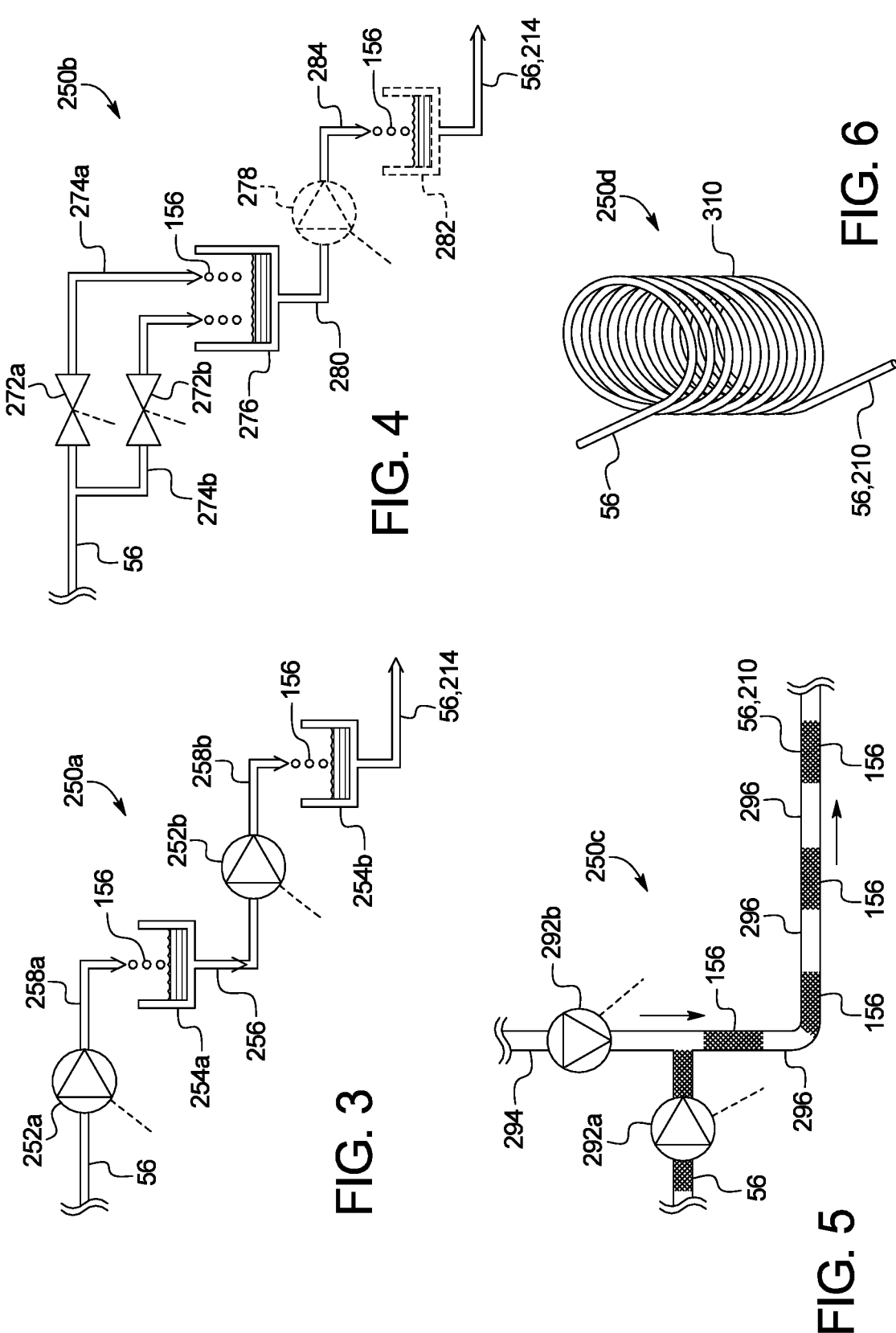
FIG. 3 is a side elevation view of a first embodiment for a flow path insulator of the present disclosure.
FIG. 4 is a side elevation view of a second embodiment for a flow path insulator of the present disclosure.
FIG. 5 is a side elevation view of a third embodiment for a flow path insulator of the present disclosure.
FIG. 6 is a side elevation view of a fourth embodiment for a flow path insulator of the present disclosure.

Referring now to FIG. 3, in a first flow path insulator embodiment, peritoneal dialysis system 10 provides flow path insulator 250a, which includes a first pump 252a positioned and arranged to pump used dialysis fluid through drain line 56 to a first chamber 254a and a second pump 252b positioned and arranged to pump used dialysis fluid from an outlet 256 of first chamber 254a to a second chamber 254b. The separation of drain line 56 from first chamber 254a, the separation of outlet 256 from second chamber 254b, and the separation of first and second chambers 254a and 254b from each other create the flow segments 156.

First and second pumps 252a and 252b may be of the same or different type as each other and the same or different type as the primary pumps 44 of cycler 20, and may for example be peristaltic pumps or gear pumps operating with drain line 56. First pump 252a in one embodiment is the primary pumps 44 of cycler 20. In various implementations of the first embodiment (i) first and second pumps 252a and 252b and first and second chambers 254a and 254b are each provided at cycler 20; (ii) first and second pumps 252a and 252b and first chamber 254a are provided at cycler 20, while second chamber 254b is provided along drain line 56, at the dialysis fluid preparation unit, or at water purifier 210; (iii) first pump 252a is provided at cycler 20, while second pump 252b and first and second chambers 254a and 254b are provided along drain line 56, at the dialysis fluid preparation unit, or at water purifier 210; or (iv) first and second pumps 252a and 252b and first and second chambers 254a and 254b are each provided along drain line 56, at the dialysis fluid preparation unit, or at water purifier 210. Second chamber 254b may accordingly output to general drain line 56 or to water purifier drain line 214 as illustrated in FIG. 3.

In various implementations, first and second chambers 254a and 254b may be cylindrical or have an oblong shape. First and second chambers 254a and 254b may form a volume, for example, from 20 milliliters ("ml") to 200 ml. Outlet 256 may have the same diameter as drain line, for example, eight millimeters ("mm"), or be larger or smaller to allow for a greater or restricted flowrate as needed. Outlet lines 258a and 258b from respective pumps 252a and 252b may extend and attach to the tops (not illustrated and perhaps not provided) of chambers 254a and 254b, but as illustrated, do not extend into a fluid level maintained within chambers 254a and 254b so as to allow the formation of flow segments 156. To this end, level sensors (not illustrated, e.g., capacitive or optical sensors) may be provided (e.g., in or along one or more of cycler 20, drain line 56, the dialysis preparation unit, or water purifier 210) to ensure that a desired drain fluid level is maintained in chambers 254a and 254b.

First and second pumps 252a and 252b under control of control unit 22 or 212 are operated to maintain a desired drain fluid level in chambers 254a and 254b. Pumps 252a and 252b may also be stopped and started on some desired periodic basis to help create flow segments 156. Additionally or alternatively, control unit 22 or 212 operates first and second pumps 252a and 252b in two alternating states, wherein (i) pump 252a is running, while pump 252b is stopped, creating an air gap between the outlet of tube 258b and the fluid surface in second chamber 245b, while chamber 254b gravity drains, and (ii) pump 252a is stopped, while pump 252b is running to empty chamber 254a into chamber 254b, while chamber 254b continues to drain, creating an air gap between the outlet of tube 258a and the fluid surface in first chamber 254a. Such a sequence guarantees an air gap at all times and a constant drain flow from chamber 254b assuming that flow path insulator 250a is operated so at to prevent chamber 254b from emptying completely.

Referring now to FIG. 4, in a second flow path insulator embodiment, peritoneal dialysis system 10 provides flow path insulator 250b, which includes a first valve 272a operable with a first fluid line 274a and a second valve 272b operable with a second fluid line 274b. First and second fluid lines 274a and 274b lead to a chamber 276. System 10 operating flow path insulator 250b is configured to sequence first and second valves 272a and 272b to create flow segments 156. FIG. 4 also illustrates that flow path insulator 250b optionally (dashed lines) includes a pump 278 positioned and arranged to pump used dialysis fluid from an outlet 280 of chamber 276 to a second chamber 282.

Valves 272a and 272b and pump 278 may be of the same or different type as the valves and primary pumps 44 of cycler 20. Pump 278 may for example be a peristaltic or gear pump operating with drain line 280. In various implementations of the second embodiment (i) first and second valves 272a and 272b, pump 278 and first and second chambers 276 and 282 are each provided at cycler 20; (ii) first and second valves 272a and 272b and first chamber 276 are provided at cycler 20, while pump 278 and second chamber 282 are provided along drain line 56, at the dialysis fluid preparation unit, or at water purifier 210; (iii) first and second valves 272a and 272b are provided at cycler 20, while pump 278 and first and second chambers 276 and 282 are provided along drain line 56, at the dialysis fluid preparation unit, or at water purifier 210; or (iv) first and second valves 272a and 272b, pump 278 and first and second chambers 276 and 282 are each provided along drain line 56, at the dialysis fluid preparation unit, or at water purifier 210. Line 284 or chamber 282 may accordingly output to general drain line 56 or to water purifier drain line 214 as illustrated in FIG. 4.

In various implementations, first and second chambers 276 and 282 may have any of the structure, functionality and alternatives discussed above for first and second chambers 254a and 254b of flow path insulator 250a. Lines 274a and 274b extend from drain line 56 (and thus may have the same dimensions) and may extend and attach to the top (not illustrated and perhaps not provided) of chamber 276, but as illustrated, do not extend into a fluid level maintained within chamber 276 so as to allow the formation of flow segments 156. The same holds true for the outlet line 284 from optional pump 278. To this end, level sensors (not illustrated, e.g., capacitive or optical sensors) may be provided (e.g., in or along one or more of cycler 20, drain line 56, the dialysis preparation unit, or water purifier 210) to ensure that a desired drain fluid level is maintained in chambers 276 and 282.

First and second valves 272a and 272b under control of control unit 22 or 212 are sequenced to create flow segments 156 extending from lines 274a and 274b, respectively, while allowing the drain flowrate to be relatively constant. Pump 278 is operated to maintain a desired drain fluid level in chamber 282. Pump 278 may also be stopped and started on some desired periodic basis to help or additionally create flow segments 156.

In an alternative implementation of 250b, only a single valve, e.g., valve 272a, is provided and control unit 22 or 212 operates valve 272a and pump 278 in two alternating states, wherein (i) valve 272a is open, while pump 278 is stopped, creating an air gap between pump 278 and second chamber 282, while chamber 282 drains or (ii) valve 272a is closed, while pump 278 is running to empty first chamber 276 into second chamber 282, while second chamber 282 continues to drain, creating an air gap between valve 272a and first chamber 276. Such a sequence guarantees an air gap at all times and a constant drain flow from chamber 282 assuming that flow path insulator 250b is operated so at to prevent chamber 282 from emptying completely.

Referring now to FIG. 5, in a third flow path insulator embodiment, peritoneal dialysis system 10 provides flow path insulator 250c, which includes a first pump 292a positioned and arranged to pump used dialysis fluid through the drain line 56 and a second pump 292b positioned and arranged to introduce air or water along an air or water line 294 into the drain line 56, creating air or water segments 296 that separate the used dialysis fluid or effluent into flow segments 156. Air or water line 294 accordingly leads from a water source, such as water purifier 210 or a tank of water, or from an air source, e.g., from ambient air separated by a hydrophobic filter that purifies the air introduced into drain line 56. Air or water line 294 may be of the same size and material as drain line 56.

In various implementations of flow path insulator 250c, drain fluid pump 292a is provided at cycler 20 and is one of the primary fluid pumps 44 of the cycler. Here, second (water or air) pump 292b may also be provided at cycler 20 or be provided by the water purifier 210, the dialysis fluid preparation unit, or along drain line 56. In alternative implementations, fluid pump 292a is provided at water purifier 210, the dialysis fluid preparation unit, or along drain line 56. If air is introduced into line 194, pump 292b may be an air pump that pumps purified air into drain line 56. If water is introduced into line 194, pump 292b may be a peristaltic or gear pump.

First and second pumps 292a and 292b under control of control unit 22 or 212 are operated to produce alternating slugs of used dialysis fluid and slugs 296 of water or air to create flow segments 156. The alteration is performed at a desired frequency to create slugs of desired length. If water is used, the water is deionized so that the water is not conductive, thereby creating non-conductive slugs. The water may be deionized via a standalone deionization device, such as one involving a deionizing filter, capacitive deionization mechanism or electrodeionization mechanism. Deionization may be provided alternatively as part of water purifier 210.

Referring now to FIG. 6, in a fourth flow path insulator embodiment, peritoneal dialysis system 10 provides flow path insulator 250d, which includes a coiled length of tubing 310 configured to create flow segments 156. Coiled length of tubing 310 may be disposable and located downstream from cycler 20 along drain line 56 or be reusable and located, e.g., inside cycler 20, inside water purifier 210 or inside the dialysis preparation unit. A ratio of the length (L) of coil 310 to a cross-sectional area (A) of coil 310 is, for example, 10,000:8 (e.g., 10 m of 8 mm inner diameter tubing), which is chosen such that the electrical resistance within coil 310 reduces any leakage current through patient line 50 and drain line 56 to an insignificant or safe level. Coil may also form air pockets naturally in the drain fluid, creating flow segments 156 as illustrated.

FIG. 6 illustrates tubing coil 310 as being vertically disposed. Here, effluent flow may be from top to bottom or bottom to top. Alternatively, tubing coil 310 may be horizontally disposed or disposed at some angle.

Referring now to FIG. 7, in a fifth flow path insulator embodiment, peritoneal dialysis system 10 provides flow path insulator 250e, which includes a peristaltic pump 322 configured to create flow segments 156. Rotor 324 extending to rollers 326 is configured to totally occlude drain line tubing segment 328 against race 330 in one or more places to create segments 156. Rollers 326 may be spring-loaded via springs 332 to help ensure that drain line tube segment 328 is fully occluded against race 330. The number of rollers 326 may also be increased as illustrated to create additional effluent segments 156. Peristaltic pump 322 may be located at cycler 20, along drain line 56, at water purifier 210 (e.g., enter tubing segment 328 via general drain line 56 and exit to the house drain via water purifier drain line 214), or at the dialysis preparation unit. Tubing segment 328 may be reusable or disposable.

Referring now to FIG. 8, in a sixth flow path insulator embodiment, peritoneal dialysis system 10 provides flow path insulator 250f, which includes a pump 342 pumping effluent along drain line 56 to an aspirator 344 configured to create flow segments 156. A chamber 346 is provided and is configured to collect flow segments 156 from aspirator 344. Aspirator 344 in the illustrated embodiment is provided in the form of a nozzle having multiple openings that create a spray or mist of flow segments 156. Chamber 346 may have any of the structure, functionality and alternatives discussed above for first and second chambers 254a and 254b of flow path insulator 250a.

Pump 342 may be one of the primary pumps 44 of cycler 20 and may be a peristaltic or gear pump. In various implementations of flow path insulator 250f (i) pump 342, aspirator 344 and chamber 346 are each provided at cycler 20; (ii) pump 342 is provided at cycler 20, while aspirator 344 and chamber 346 are provided at water purifier 210 (e.g., enter pump 342 via general drain line 56 and exit chamber 346 via water purifier drain line 214), at dialysis fluid preparation unit, or along drain line 56; or (iii) pump 342, aspirator 344 and chamber 346 are each provided at water purifier 210, at dialysis fluid preparation unit, or along drain line 56.

It should be appreciated that flow segments 156 may be sized differently. Flow segments 156 may (i) be very small in size or diameter, e.g., the size of a mist particle for the aspirator flow path insulator 250f, (ii) be larger slugs of used dialysis fluid, e.g., as with insulator 250c of FIG. 5, or (iii) be chamber sized as with the chambers of insulators 250a and 250b.

Referring now to FIG. 9, in a seventh flow path insulator embodiment, peritoneal dialysis system 10 provides flow path insulator 250g, which includes siphons 352 and 358 configured to create the flow segments. First siphon 352 in the illustrated embodiment includes a siphon tube 354 and a siphon chamber 356. Second siphon 358 includes a second siphon tube 360 and a second siphon chamber 362. First siphon 352 outputs to the second siphon 358 in such a way that siphon tube 354 does not contact a fluid level residing in second chamber 362 of second siphon 358, which may create flow segments 156. The bottom of first siphon tube 354 may attach to a top (not illustrated) of second siphon chamber 362 but does not extend through the top at all or enough to contact the liquid level therein. In a similar manner, drain line 56 does not contact the fluid level within first siphon chamber 356, possibly creating flow segments 156.

Siphons 352 and 358 may be reusable or disposable. Siphon chambers 356 and 362 may include any of the structure, functionality and alternatives discussed above for first and second chambers 254a and 254b of flow path insulator 250a. Siphon tubes 354 and 360 may be rigid or flexible, and be made of any of the metals or polymers discussed herein. In various implementations, siphons 352 and 358 may be located within cycler 20, within water purifier 210 (e.g., enter chamber 356 via general drain line 56 and exit chamber 362 via water purifier drain line 214), within dialysis fluid preparation unit, or along drain line 56.

The sizes of siphon tubes 354 and 360 and siphon chambers 356 and 362 are selected such that siphons 352 and 358 create discontinuous flow. Initially, as siphon chambers 356 and 362 begin to fill, e.g., via the primary pumps 44 of cycler 20, no flow exits siphon tubes 354 and 360. When the head pressure of effluent within siphon chambers 356 and 362 increases to a threshold level, effluent flows out of siphon tubes 354 and 360.

In one implementation, first and second siphons 352 and 358 operate in first and second states. In a first state, effluent flows from cycler 20 to chamber 356 of first siphon 352, filling first siphon chamber 356, building head pressure, while second siphon chamber 362 drains, losing head pressure. Here, an effluent air gap exists between the first and second siphon chambers 356 and 362. In a second state, effluent still flows from cycler 20 to chamber 356 of first siphon 352, but here first siphon chamber 356 drains, losing head pressure, while siphoning does not take place in chamber 362 of second siphon 358 because the level of fluid in chamber 362 has fallen below at least the highest point of outlet 360, interrupting the siphoning. In the second state, the effluent gap exists between chamber 362 of second siphon 358 and the house drain. To create the first and second states in one embodiment, (i) the first siphon 352 is configured to drain at a flowrate greater than the drain flowrate from cycler 20 to the first siphon, and (ii) first and second siphons 352 and 358 are configured such that their switch states between building vs. losing head pressure for first siphon 352 and losing vs. building head pressure for second siphon 358, and vice versa, occur at the same time or substantially the same time.

Referring now to FIG. 10, in an eighth flow path insulator embodiment, peritoneal dialysis system 10 provides flow path insulator 250h, which includes a valve 372 selectively allowing effluent flow, e.g., via the primary pumps 44 of cycler 20, through a first chamber 374 having an output line 376 directed towards, but separate from, a second chamber 380 to create the flow segments 156. First chamber 374 outputs via line 376 and a second valve 378 to a second chamber 380 in such a way that output line 376 does not contact a fluid level residing in second chamber 380. Valves 372 and 378 may be toggled to create flow segments 156.

That is, the bottom of output line 376 may attach to a top (not illustrated) of second chamber 380 but does not extend through the top at all or enough to contact the liquid level therein. In a similar manner, drain line 56 does not contact the fluid level within first chamber 374, further creating flow segments 156. Valve 372 may also be toggled on and off to help create discontinuous flow.

First and chambers 374 and 380 may have any of the structure, functionality and alternatives discussed above for first and second chambers 254a and 254b of flow path insulator 250a. In various implementations of flow path insulator 250h (i) valves 372 and 378, first chamber 374 and second chamber 380 are each located at cycler 20; (ii) valves 372 and 378 and first chamber 374 are located at cycler 20, while second chamber 380 is located at water purifier 210 (e.g., effluent enters first chamber 374 via general drain line 56 and exits second chamber 380 via water purifier drain line 214), at dialysis fluid preparation unit, or along drain line 56; (iii) valve 372 is located at cycler 20, while first chamber 374, second valve 378 and second chamber 380 are located at water purifier 210, at dialysis fluid preparation unit, or along drain line 56; or (iv) valves 372 and 378, first chamber 374 and second chamber 380 are each located at water purifier 210, at dialysis fluid preparation unit, or along drain line 56.

Additionally or alternatively, control unit 22 or 212 operates first and second valves 372 and 378 in two alternating states, wherein (i) valve 372 is open, while valve 378 is closed, creating an air gap between chambers 374 and 380, while chamber 380 gravity drains or (ii) valve 372 is closed, while valve 378 is open to empty chamber 374 into chamber 380, while chamber 380 continues to drain, creating an air gap between valve 372 and first chamber 374. Such a sequence guarantees an air gap and a constant drain flow from second chamber 380 assuming that flow path insulator 250h is operated so as to prevent second chamber 380 from emptying completely.

Figures 11, 12:
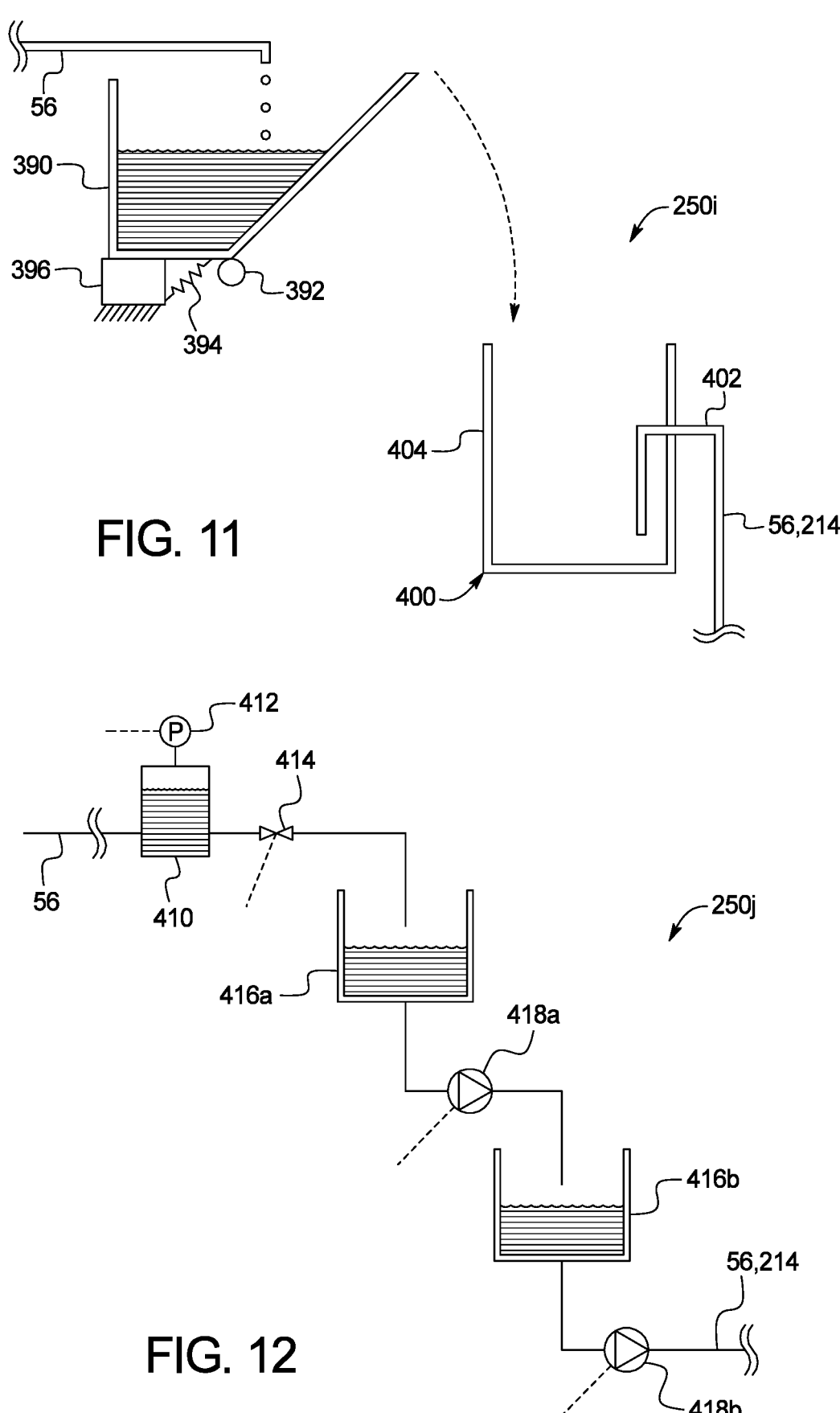
FIG. 11 is a side elevation view of a ninth embodiment for a flow path insulator of the present disclosure.
FIG. 12 is a side elevation view of a tenth embodiment for a flow path insulator of the present disclosure.

Referring now to FIG. 11, in a ninth flow path insulator embodiment, peritoneal dialysis system 10 provides flow path insulator 250i, which includes a first chamber 390 that receives effluent from drain line 56. First chamber 390 is hinged along a hinge 392 located at the bottom of first chamber 390. First chamber 390 is structured to reside in the upright position illustrated in FIG. 11 under its own weight alone. First chamber 390 may also be counterweighted such that it returns to the upright position illustrated in FIG. 11 after tipping and delivering dialysis fluid to siphon 400. If needed, a biasing device 394, such as a spring, may be provided and extend between first chamber 390 and a stop 396 to help return first chamber 390 to the upright position illustrated in FIG. 11 after dialysis fluid delivery.

Flow path insulator 250i also includes a siphon 400. Siphon 400 in the illustrated embodiment includes a siphon tube 402 and a siphon chamber 404. Siphon 400 outputs to drain line 62 or 214. Chamber 390 and siphon 400 may be reusable or disposable. Chamber 390 and siphon chamber 404 may include any of the structure, functionality and alternatives discussed above for first and second chambers 254a and 254b of flow path insulator 250a. Siphon tube 402 may be rigid or flexible, and be made of any of the metals or polymers discussed herein. In various implementations, chamber 390 and siphon 400 may be located within cycler 20, within water purifier 210 (e.g., enter chamber 390 via general drain line 56 and exit siphon chamber 404 via water purifier drain line 214), within dialysis fluid preparation unit, and/or along drain line 56.

In operation, chamber 390 fills with effluent while effluent drains from siphon chamber 404 to house drain. Here, an air gap is created between rotatable chamber 390 and siphon chamber 404. At some point before rotatable chamber 390 tips, the head pressure within draining siphon chamber 404 falls to a point such that effluent no longer flows from siphon chamber 404, creating an air gap between siphon chamber 404 and the house drain. When the weight of effluent becomes great enough to overcome the counterweight of chamber 390 and/or force of biasing device 394, rotatable chamber 390 tips and rotates about hinge 392. The effluent is quickly released from chamber 390 into siphon chamber 404.

Although not illustrated, when rotatable chamber 390 tips, an electrical contact located between the bottom of chamber 390 and the top of stop 396 is broken, which triggers control unit 22 of cycler 20 to momentarily stop fluid pump chambers 44 during the current drain, so that effluent does not spill around the outside of chamber 390. If flow path insulator 250i is located for example within water purifier 210, the trigger due to the breaking of the electrical contact causes control unit 212 of water purifier 210 to send a signal wired or wirelessly to control unit 22 of cycler 20, which then temporarily stops pump chambers 44. The electrical contact can alternatively be any type of switch that switches from a first state to a second state when chamber 390 is tipped, and which returns to the first state when chamber 390 is returned to its upright position.

The transfer of effluent from chamber 390 to siphon chamber 404 occurs quickly, such that an associated drain flow interruption is short. Once the weight of the effluent is removed from rotatable chamber 390, chamber 390 under its own counterweight (and/or with the help of biasing device 394, e.g., a spring) rotates about hinge 392 back into its upright position, remaking the electrical contact with the lead or electrode located on stop 396, which in turn triggers control unit 22 to resume the actuation of pump chamber 44 to continue the current drain. Siphon chamber 404 after being filled with effluent from rotatable chamber 390 has the requisite head pressure to remove effluent to house drain.

Referring now to FIG. 12, in a tenth flow path insulator embodiment, peritoneal dialysis system 10 provides flow path insulator 250j, which includes a container or bag 410 located along drain line 56 upstream of a valve 414, which allows or does not allow effluent to flow to a first chamber 416a. A pressure sensor 412 is positioned to read a pressure inside container or bag 410 and output a signal corresponding to that pressure to one or both of control unit 22 or control unit 212. First chamber 416a is separated from a second chamber 416b by a first pump 418a. In various implementations, first and second chambers 416a and 416b may have any of the structure, functionality and alternatives discussed above for first and second chambers 254a and 254b of flow path insulator 250a.

A second pump 418b is located downstream from second chamber 416b. First and second pumps 418a and 418b may be of the same or different type as each other and the same or different type as the primary pumps 44 of cycler 20, and may for example be peristaltic pumps or gear pumps operating with drain line 56. First pump 418a in one embodiment includes the primary pumps 44 of cycler 20. In various implementations of the first embodiment (i) first and second pumps 418a and 418b and first and second chambers 416a and 416b are each provided at cycler 20; (ii) first and second chambers 416a and 416b and first pump 252a are provided at cycler 20, while second pump 418b is provided along drain line 56, at the dialysis fluid preparation unit, or at water purifier 210; (iii) first chamber 416a is provided at cycler 20, while second chamber 416b and first and second pumps 418a and 418b are provided along drain line 56, at the dialysis fluid preparation unit, or at water purifier 210; or (iv) first and second pumps 418a and 418b and first and second chambers 416a and 416b are each provided along drain line 56, at the dialysis fluid preparation unit, or at water purifier 210. Second pump 418b may accordingly output to general drain line 56 or water purifier drain line 214 as illustrated in FIG. 12.

The operation of flow path insulator 250j in one embodiment includes operating cycler 20 to drain patient P as illustrated in FIG. 1 to container or bag 410, while valve 414 is maintained in a closed or no-flow state. At the same time, first pump 418a pumps fluid from first chamber 416a to second chamber 416b, while second pump 418b is not actuated. When the effluent level in first chamber 416a falls below some threshold level, e.g., (i) as measured by a level or weight sensor (not illustrated) outputting to at least one control unit 22 or 212, and/or (ii) by monitoring how much effluent has been removed from first chamber 416a, first pump 418a is stopped, e.g., slightly before, valve 414 is opened (to be sure there is no delay giving electrical contact to earth) and, filling first chamber 416a, e.g., via gravity, from container or bag 410. Second pump 418b is then actuated to pump effluent from second chamber 416b to house drain via drain line 56 or 214. When the level of effluent in first chamber 416a reaches an upper threshold (e.g., via level sensor, weight sensor and/or volume monitoring), valve 414 is closed, second pump 418b is stopped, and the above cycle is repeated with first pump 418a emptying effluent from first chamber 416a into second chamber 416b. The above sequence ensures that an air gap always exists (either second pump 418b or first pump 416a is stopped) between patient P and the house drain 56.

At any time while valve 414 is closed, pumps 44 of cycler 20 may be used to refill container or bag 410 with effluent. Pumps 44 of cycler 20 operate at a flowrate prescribed for the patient in one embodiment. Pumps 418a and 418b operate at a flowrate sufficient to ensure that first and second chambers 416a and 416b, respectively, do not overflow. Pressure sensor 412 ensures that container or bag 410 does not become overpressurized. Pressure sensor 412 may also be used for control unit 22 or 212 to know when to open valve 414 in the sequence described above.

Figure 13A:
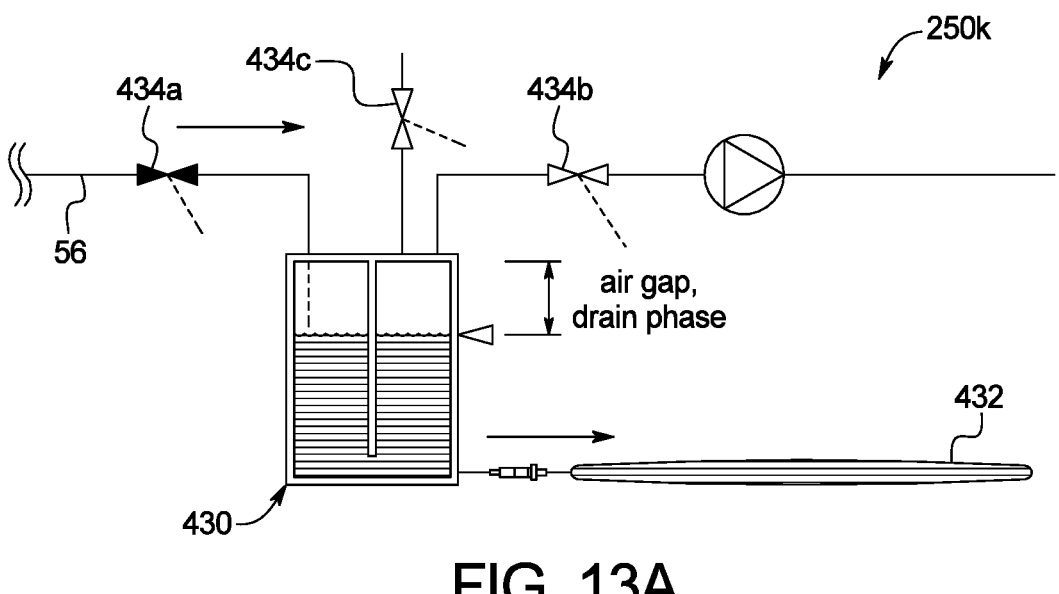
FIGS. 13A and 13B are side elevation views of an eleventh embodiment for a flow path insulator of the present disclosure.
Figure 13B:
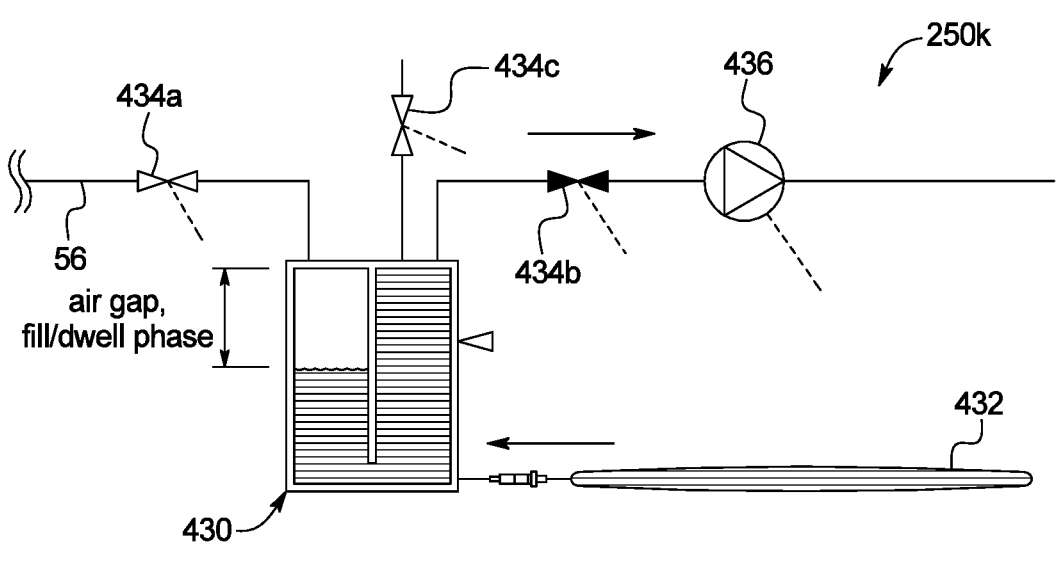

Referring now to FIGS. 13A and 13B, in an eleventh flow path insulator embodiment, peritoneal dialysis system 10 provides flow path insulator 250k. Flow path insulator 250k takes advantage of the different phases involved with peritoneal dialysis, namely, the drain, fill and dwell phases. Flow path insulator 250k is used while cycler 20 performs a full drain and stores the effluent until the drain phase is completed, after which cycler 20, water purifier 210, a dialysis fluid preparation unit or other pump removes the effluent to the house drain during the fill and/or dwell phases. In particular, FIGS. 13A and 13B illustrate that a chamber 430 is provided along drain line, either at cycler 20, along the drain line 56 between cycler 20 and the house drain, at water purifier 210, or at the dialysis fluid preparation unit. A drain container or bag 432 is placed in fluid communication with chamber 430. Drain container or bag 432 may hold three liters of effluent or otherwise be large enough to accept an entire drain volume from patient P including an associated ultrafiltration volume. In various embodiments chamber 430 is reusable and is made of any of the materials described herein, while drain container or bag 432 is disposable and is made of any of the materials described herein.

Valves 434a and 434b are provided in the illustrated embodiment upstream and downstream, respectively, of chamber 430. A third valve 434c may be provided as a vent valve. Pump 436 is located downstream of valve 434b (but could be located upstream of the valve) and may be of any type of pump discussed herein. Valves 434a to 434c and pump 436 may be provided at cycler 20, along the drain line 56 between cycler and the house drain, at water purifier 210, or at the dialysis fluid preparation unit. If provided at water purifier 210, drain line 56 outputs to water purifier drain line 214.

FIG. 13A illustrates that during a drain phase, valve 434a is open, while valves 434b and 434c are closed. Pump 436 is not operated. Effluent is pumped into chamber 430 and flows from the chamber into drain container or bag 432. An air gap is maintained between the entry point of effluent into chamber 430 and the chamber level.

FIG. 13B illustrates that after the drain phase, during the fill and/or dwell phase, valve 434b is open, while valves 434a and 434c are closed. Chamber 430 as illustrated includes a divider, which forces effluent on the intake side of the divider to flow down beneath the divider before being pulled out of the output side of the chamber via pump 436, thereby maintaining the air gap. Pump 436 pulls effluent from container or bag 432 to the house drain while valve 434a is closed. Both the air gap and the closure of valve 434a ensure that no current can flow between patient P and the house drain.

Figure 14:
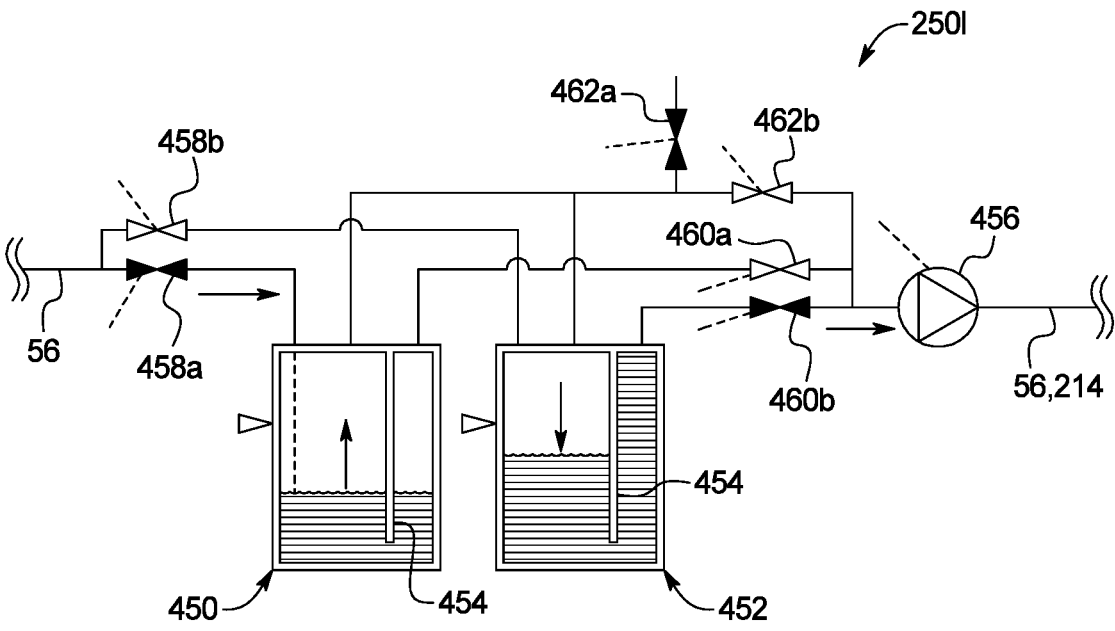
FIG. 14 is a side elevation view of a twelfth embodiment for a flow path insulator of the present disclosure.

Referring now to FIG. 14, in a twelfth flow path insulator embodiment, peritoneal dialysis system 10 provides flow path insulator 250l. FIG. 14 illustrates that chambers 450 and 452 are provided along drain line, either at cycler 20, along the drain line 56 between cycler 20 and the house drain, at water purifier 210, or at the dialysis fluid preparation unit. Chambers 450 and 452 may be reusable and be made of any of the materials described herein. Chambers 450 and 452 each include a divider 454 as described above for chamber 430, which forces effluent entering the chambers down beneath the divider and then up and out of an outlet of the chambers. Chambers 450 and 452 as discussed below operate in parallel with each other and are spliced between inlet drain line 56 and pump 456, which may be of any of the types of pumps discussed herein.

Flow path insulator 250l includes six valves including inlet valves 458a and 458b, outlet valves 460a and 460b and vent valve 462a and tank valve 462b. Inlet valve 458a and outlet valve 460b form a first parallel path, while inlet valve 458b and outlet valve 460a form a second parallel path. Inlet valve 458a runs to chamber 450, while inlet valve 458b runs to chamber 452. Outlet valve 460a extends from chamber 450, while outlet valve 460b extends from chamber 452. Vent valve 462a operates to vent air from chambers 450 and 452 when filled. Tank valve 462b is used at the end of an emptying phase to thereafter equalize the level in the two halves of the emptied chamber.

In operation, control unit 22 or 212 sequences the operation of the valves of one parallel path to fill one of chambers 450 or 452, while the other of the chambers is emptied to house drain. In FIG. 14, inlet valve 458a of the first parallel path is open to allow cycler pumps 44 to push effluent into chamber 450, while inlet valve 458b of the second parallel path is closed. At the same time, outlet valve 460b of the second parallel path is open to allow pump 456 to pump effluent from chamber 452 to the house drain, while outlet valve 460a of the first parallel path is closed.

The level of effluent in each chamber 450 and 452 is known via at least one of (i) one or more level sensor operating with each chamber and outputting to at least one of control unit 22 or 212, (ii) a weigh scale operating with each chamber and outputting to at least one of control unit 22 or 212, and/or (iii) monitoring a volume of effluent pumped to or from the chambers, e.g., based on the accuracy of the pump, such as counting known stroke volumes. In one embodiment, control unit 22 or 212 is programmed so that the low level limit of a chamber being drained is reached at the same time that an upper level limit of the other being filled is reached. It may be preferable however that control unit 22 or 212 is programmed such that the draining time for chambers 450 and 452 is shorter than the filling time.

In varying embodiments, both lower (draining) and upper (filling) limits have to be reached before switching the valve states. Here, it may be desirable to run pump 456 faster than cycler pumps 44 to ensure that flow path insulator 250l is always filling one of chambers 450 or 452. In an alternative embodiment, only one of the lower (draining) or upper (filling) limits is reached before switching the valve states. Here, filling may occur faster than draining, wherein cycler pumps 44 may be stopped, if needed, while cycler 20 waits for the emptying of chamber 450 or 452 to be completed.

Whatever the valve switch state trigger may be, when it is reached in FIG. 14, control unit 22 or 212 switches the inlet and outlet valve states. Here, inlet valve 458b of the second parallel path is open to allow cycler pumps 44 to push effluent into chamber 452, while inlet valve 458a of the first parallel path is closed. At the same time, outlet valve 460a of the first parallel path is open to allow pump 456 to pump effluent from chamber 450 to the house drain, while outlet valve 460b of the second parallel path is closed.

An air gap always exists with flow path insulator 250l because the fluid path running from cycler 20 (and patient P) flows to one of chambers 450 or 452, while the fluid path from the chambers to the house drain flows from the other of chambers 452. Chambers 450 and 452 also maintain air gaps as illustrated, providing additional electrical current isolation.

Figure 15:
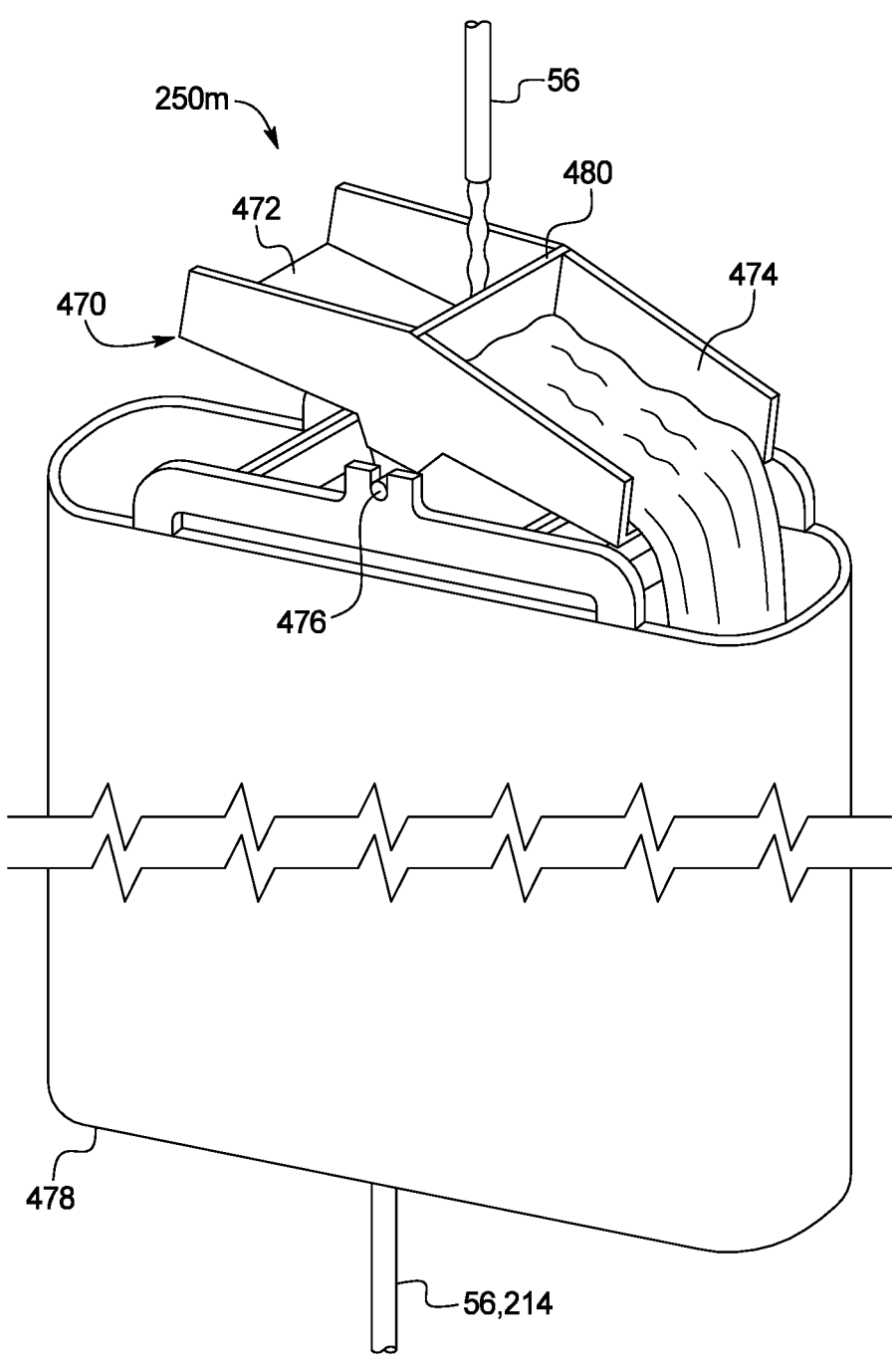
FIG. 15 is a perspective view of a thirteenth embodiment for a flow path insulator of the present disclosure.

Referring now to FIG. 15, in a thirteenth flow path insulator embodiment, peritoneal dialysis system 10 provides flow path insulator 250m. FIG. 15 illustrates that flow path insulator 250m is provided along the drain line, either at cycler 20, along the drain line 56, 214 between cycler 20 and the house drain, at water purifier 210, or at the dialysis fluid preparation unit. Flow path insulator 250m may be reusable and be made of any of the materials described herein. Flow path insulator 250m includes a pivoting device or cradle 470, which includes compartments 472 and 474 that pivots back and forth about a pivot 476 under the weight of incoming used dialysis fluid or effluent from drain line 56. Used dialysis fluid flows continuously along a drain line 56 and into a container 478 connected to or formed with pivoting device or cradle 470 located at the top of container 478.

Compartments 472 and 474 are separated by a middle wall 480. Used dialysis fluid falling into cradle 470 impinges or contacts one side or the other of a middle wall 480 separating cradle 470 into compartments 472 and 474. In FIG. 15, the side of wall 480 that is currently being contacted by falling effluent belongs to compartment 472, which is being filled. Simultaneously, compartment 474 is emptying used dialysis fluid into container 478. It should be appreciated that in the state shown in FIG. 15, compartment 472 is isolated from earth ground at the end of the drain line 56, 214. The side of wall 480 in FIG. 15 that is not currently being contacted by falling effluent belongs to compartment 474, which is draining into container 478, which in turn drains to the distal end of the drain line 56, 214 and to house drain. If needed, a separate pump (not illustrated) may be provided to pump from container 478 to house drain. It should be appreciated that compartment 474 in the state of FIG. 15 is isolated from the patient.

When enough effluent enters compartment 472 in combination with enough effluent leaving compartment 474, pivoting device or cradle 470 switches states and pivots about pivot 476. At that point, compartment 472 drains effluent and is isolated electrically from the patient, while compartment 474 is filled with effluent and is isolated electrically from earth ground. The state switching is repeated, allowing effluent to drain continuously from drain line 56 into cradle 470, until the patient drain is completed.

Additional Incoming Fluid Streams

Figure 16:
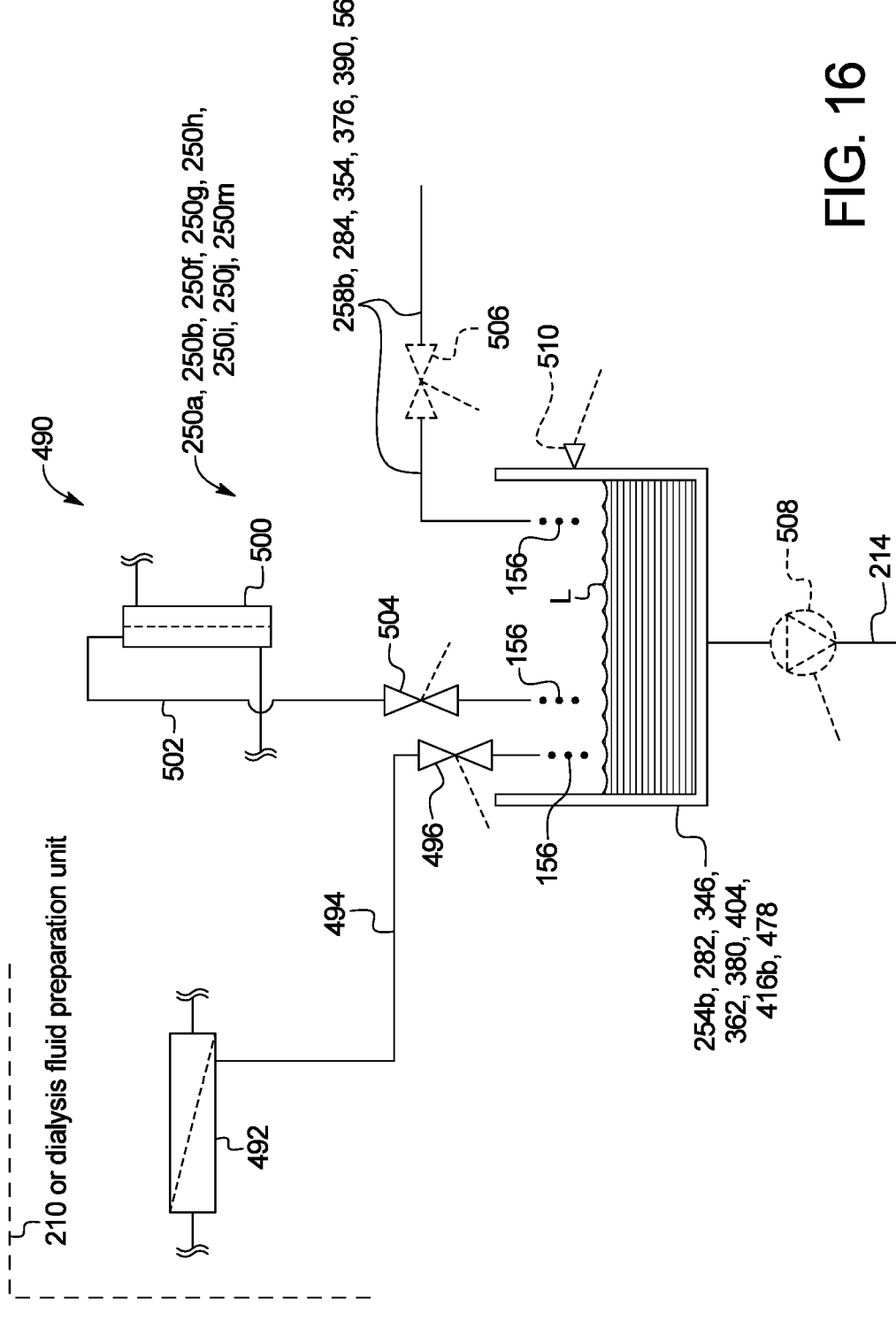
FIG. 16 is a side elevation view of an alternative implementation of multiple flow path insulator embodiments discussed herein, wherein as part of a water purifier or dialysis fluid preparation unit, one of the chambers receives at least one additional incoming fluid stream, e.g., a water purification device reject stream.

Referring now to FIG. 16, an alternative implementation 490 of flow path insulators 250*a*, 250*b*, 250*f*, 250*g*, 250*h*, 250*i*, 250*j* and 250*m* is illustrated. The alternative implementation may be provided when the above-listed flow path insulators are installed with water purifier 210 or a dialysis fluid preparation unit. Here, respective outlet line 258*b*, outlet line 284, the outlet line from pump 332, siphon tube 354, output line 376, rotatable chamber 390, the outlet line from pump 418*a*, or drain line 56 lead respectively into second chamber 254*b*, chamber 282, chamber 346, chamber 362, second chamber 380, siphon chamber 404, second chamber 416*b*, or container 478.

Implementation 490 of FIG. 16 includes additional lines that lead to second chamber 254*b*, chamber 282, chamber 346, chamber 362, second chamber 380, siphon chamber 404, second chamber 416*b*, or container 478, namely, reject lines from water purification devices, which may be provided with water purifier 210 or a water purification portion of the dialysis fluid preparation unit. The water purification device may be of any type having a reject fluid or water line. There may be any desired number of water purification devices each having a reject line leading to second chamber 254*b*, chamber 282, chamber 346, chamber 362, second chamber 380, siphon chamber 404, second chamber 416*b*, or container 478.

In the illustrated embodiment, one water purification device is a reverse osmosis unit 492 having a fluid or water reject line 494 leading to second chamber 254*b*, chamber 282, chamber 346, chamber 362, second chamber 380, siphon chamber 404, second chamber 416*b*, or container 478. Reject fluid or water is selectively allowed to flow to the chamber via a valve 496 (e.g., electrically actuated solenoid valve) under control of control unit 212 of water purifier 210 or the control unit of the dialysis fluid preparation unit. Valve 496 may or may not be sequenced open and closed in an attempt to create the flow segments 156 discussed herein.

In the illustrated embodiment, anther water purification device is an ultrafilter 500 having a fluid or water reject line 502 leading to second chamber 254*b*, chamber 282, chamber 346, chamber 362, second chamber 380, siphon chamber 404, second chamber 416*b*, or container 478. Reject fluid or water is selectively allowed to flow to the chamber via a valve 504 (e.g., electrically actuated solenoid valve) under control of control unit 212 of water purifier 210 or the control unit of the dialysis fluid preparation unit. Valve 504 likewise may or may not be sequenced open and closed in an attempt to create flow segments 156.

An optional valve 506 (e.g., electrically actuated solenoid valve) under control of control unit 212 of water purifier 210 or the control unit of the dialysis fluid preparation unit may be provided along outlet line 258*b*, outlet line 284, the outlet line from pump 332, siphon tube 354, output line 376, rotatable chamber 390, the outlet line from pump 418*a*, or drain line 56. Optional valve 504 may be sequenced open and closed in an attempt to create flow segments 156 in addition to the used dialysis fluid or effluent flow separation provided by of flow path insulators 250*a*, 250*b*, 250*f*, 250*g*, 250*h*, 250*i*, 250*j* and 250*m*.

In an alternative embodiment, optional valve 506 is sequenced open and closed in an attempt to create flow segments 156 instead of the flow path separation provided by of flow path insulators 250*a*, 250*b*, 250*f*, 250*g*, 250*h*, 250*i*, 250*j* and 250*m*. Here, the sequencing of optional valve 506 forming flow path segments 156 is the only mechanism to create used dialysis fluid or effluent flow separation.

In another alternative embodiment, the chamber in FIG. 16 is a separate, additional chamber and is not second chamber 254*b*, chamber 282, chamber 346, chamber 362, second chamber 380, siphon chamber 404, second chamber 416*b*, or container 478, respectively, of flow path insulators 250*a*, 250*b*, 250*f*, 250*g*, 250*h*, 250*i*, 250*j* and 250*m*. Water purification devices 492 and 500 and associated lines 494 and 502 and valves 496 and 504 are again provided. Here, optional valve 506 may or may not be provided, and if provided, may or may not be sequenced open and closed in an attempt to create flow segments 156. The additional chamber and optional valve 506 in this alternative embodiment may be provided and used alternatively with air/water injection flow path insulator 250*c*, coil tube flow path insulator 250*d*, peristaltic pump flow path insulator 250*e*, flow path insulator 250*k* and flow path insulator 250*l*.

In a further alternative embodiment, the chamber in FIG. 16 is instead first chamber 254*a* of flow path insulator 250*a*, first chamber 276 of flow path insulator 250*b*, first siphon chamber 356 of flow path insulator 250*g*, first chamber 374 of flow path insulator 250*h*, rotatable chamber 390 of flow path insulator 250*i*, first chamber 416*a* of flow path insulator 250*j*, chamber 430 of flow path insulator 250*k*, or either or both of first and second chambers 450, 452 of flow path insulator 250*l*. Water purification devices 492 and 500 and associated lines 494 and 502 and valves 496 and 504 are again provided. Here, optional valve 506 may or may not be provided and if provided, may or may not be sequenced open and closed in an attempt to create flow segments 156.

In any of the alternative embodiments discussed above, an optional pump 508 (e.g., peristaltic or gear pump) under control of control unit 212 of water purifier 210 or the control unit of the dialysis fluid preparation unit, if not already provided, may be provided along drain line 214 of water purifier 210 or a similar drain line of the dialysis fluid preparation unit. To drain the chamber, an optional level sensor 510 outputting to the control unit may also be provided to trigger the control unit to actuate pump 508 when the combined used dialysis fluid and reject fluid or water level L rises to meet level sensor 510.

It should be understood that various changes and modifications to the presently preferred embodiments described herein will be apparent to those skilled in the art. For example, while the figures and description generally describe a single flow path insulator 250 per a given system 10, it is contemplated to provide two or more flow path insulators as desired, at any two or more of cycler 20, water purifier 210, the dialysis fluid preparation unit, and/or along the drain line 56. Moreover, the operation of any one, or more or all of flow path insulators 250 may be via control unit 22 of cycler 20, control unit 212 of water purifier 210, or a combination thereof. Such changes and modifications may be made without departing from the spirit and scope of the present invention and without diminishing its intended advantages. It is therefore intended that such changes and modifications be covered by the appended claims.

The invention is claimed as follows:

1. A peritoneal dialysis system comprising:
a cycler;
a disposable set including a patient line and a drain line, the cycler configured to pump fresh dialysis fluid to a patient via the patient line and used dialysis fluid from the patient via the drain line;
one of (i) a water purifier for supplying purified water for mixing to form fresh dialysis fluid at the disposable set, (ii) at least one fresh dialysis fluid container provided as part of the disposable set for supplying fresh dialysis fluid, or (iii) a dialysis fluid preparation unit configured to supply fresh dialysis fluid to the disposable set; and
at least one flow path insulator provided at or by at least one of the cycler, the water purifier, the dialysis fluid preparation unit, or along the drain line, the flow path insulator configured to separate used dialysis fluid flowing along the drain line, wherein the at least one flow path insulator includes a first valve operable with a first fluid line and a second valve operable with a second fluid line, the first and second fluid lines leading to a chamber, the system configured to sequence the first and second valves to separate the used dialysis fluid to limit current flowing from the patient to a house drain.

2. The peritoneal dialysis system of claim 1, wherein the drain line extends to the water purifier so that at least a portion of the flow path insulator provided at or by the water purifier can separate used dialysis fluid flowing along the drain line.

3. The peritoneal dialysis system of claim 1, wherein the drain line extends to the dialysis preparation unit so that at least a portion of the flow path insulator provided at or by the dialysis fluid preparation unit can separate used dialysis fluid flowing along the drain line.

4. The peritoneal dialysis system of claim 1, wherein the drain line extends along the cycler so that at least a portion of the flow path insulator located at or by the cycler can separate used dialysis fluid flowing along the drain line.

5. The peritoneal dialysis system of claim 1, wherein the flow path insulator includes a first pump positioned and arranged to pump used dialysis fluid through the drain line to a first chamber and a second pump positioned and arranged to pump used dialysis fluid from an outlet of the first chamber to a second chamber, the operation of the first and second pumps separating the used dialysis fluid to limit current flowing from the patient to the house drain.

6. The peritoneal dialysis system of claim 5, wherein the first pump is provided at the cycler and the second pump is provided at or by the water purifier, the dialysis fluid preparation unit, or along the drain line.

7. The peritoneal dialysis system of claim 6, wherein the first pump is a primary pump of the cycler.

8. The peritoneal dialysis system of claim 5, wherein the first and second chambers are each provided at any of the cycler, the water purifier, the dialysis fluid preparation unit, or along the drain line.

9. The peritoneal dialysis system of claim 1, wherein the flow path insulator further includes a pump positioned and arranged to pump used dialysis fluid from an outlet of the chamber to a second chamber, the system configured to sequence the first and second valves and the operation of the pump to separate the used dialysis fluid to limit current flowing from the patient to the house drain.

10. The peritoneal dialysis system of claim 1, wherein the flow path insulator includes a peristaltic pump configured to create flow separating segments to limit current flowing from the patient to the house drain.

11. The peritoneal dialysis system of claim 1, wherein the at least one flow path insulator is provided at or by the water purifier or the dialysis fluid preparation unit, and which includes at least one water purification device having a reject line outputting to the flow path insulator.

12. The peritoneal dialysis system of claim 11, which includes at least one valve provided along the at least one respective reject line, the at least one valve sequenced open and closed to create flow path segments.

13. The peritoneal dialysis system of claim 11, wherein the at least one flow path insulator includes a valve sequenced open and closed to create flow path segments.

14. A peritoneal dialysis system comprising:
a cycler;
a disposable set including a patient line and a drain line, the cycler configured to pump fresh dialysis fluid to a patient via the patient line and used dialysis fluid from the patient via the drain line;
one of (i) a water purifier for supplying purified water for mixing to form fresh dialysis fluid at the disposable set, (ii) at least one fresh dialysis fluid container provided as part of the disposable set for supplying fresh dialysis fluid, or (iii) a dialysis fluid preparation unit configured to supply fresh dialysis fluid to the disposable set; and
at least one flow path insulator provided at or by at least one of the cycler, the water purifier, the dialysis fluid preparation unit, or along the drain line, the flow path insulator configured to separate used dialysis fluid flowing along the drain line wherein the at least one flow path insulator includes a first pump positioned and arranged to pump used dialysis fluid through the drain line and a second pump positioned and arranged to introduce air or water into the drain line to create used dialysis fluid flow separating segments to limit current flowing from the patient to a house drain.

15. The peritoneal dialysis system of claim 14, wherein the first pump is provided at the cycler and the second pump is provided at or by the water purifier, the dialysis fluid preparation unit, or along the drain line.

16. The peritoneal dialysis system of claim 14, wherein the first pump is a primary pump of the cycler.

17. A peritoneal dialysis system comprising:
a cycler;
a disposable set including a patient line and a drain line, the cycler configured to pump fresh dialysis fluid to a patient via the patient line and used dialysis fluid from the patient via the drain line;
one of (i) a water purifier for supplying purified water for mixing to form fresh dialysis fluid at the disposable set, (ii) at least one fresh dialysis fluid container provided as part of the disposable set for supplying fresh dialysis fluid, or (iii) a dialysis fluid preparation unit configured to supply fresh dialysis fluid to the disposable set; and
at least one flow path insulator provided at or by at least one of the cycler, the water purifier, the dialysis fluid preparation unit, or along the drain line, the flow path insulator configured to separate used dialysis fluid flowing along the drain line to limit current flowing from the patient to a house drain,
wherein the at least one flow path insulator includes a chamber that receives used dialysis fluid, the chamber hinged via a hinge and configured to tip via weight of the used dialysis fluid so that the used dialysis fills a siphon enough such that head pressure within the siphon causes used dialysis fluid to flow from the siphon.

18. The peritoneal dialysis system of claim 17, wherein the flow path insulator includes at least one of (i) a biasing device positioned and arranged to return the chamber to a filling position after tipping or (ii) a switch that switches from a first state to a second state when the first chamber is tipped to prevent flow of used dialysis fluid to the chamber until the switch is returned to the first state.

19. A peritoneal dialysis system comprising:
a cycler;
a disposable set including a patient line and a drain line, the cycler configured to pump fresh dialysis fluid to a patient via the patient line and used dialysis fluid from the patient via the drain line;
one of (i) a water purifier for supplying purified water for mixing to form fresh dialysis fluid at the disposable set, (ii) at least one fresh dialysis fluid container provided as part of the disposable set for supplying fresh dialysis fluid, or (iii) a dialysis fluid preparation unit configured to supply fresh dialysis fluid to the disposable set; and
at least one flow path insulator provided at or by at least one of the cycler, the water purifier, the dialysis fluid preparation unit, or along the drain line, the flow path insulator configured to separate used dialysis fluid flowing along the drain line, wherein the at least one flow path insulator includes an aspirator configured to create flow separating segments to limit current flowing from the patient to a house drain, and a chamber configured to collect the flow separating segments from the aspirator.

20. A peritoneal dialysis system comprising:
a cycler;
a disposable set including a patient line and a drain line, the cycler configured to pump fresh dialysis fluid to a patient via the patient line and used dialysis fluid from the patient via the drain line;
one of (i) a water purifier for supplying purified water for mixing to form fresh dialysis fluid at the disposable set, (ii) at least one fresh dialysis fluid container provided as part of the disposable set for supplying fresh dialysis fluid, or (iii) a dialysis fluid preparation unit configured to supply fresh dialysis fluid to the disposable set; and
at least one flow path insulator provided at or by at least one of the cycler, the water purifier, the dialysis fluid preparation unit, or along the drain line, the flow path insulator configured to separate used dialysis fluid flowing along the drain line, wherein the at least one flow path insulator includes a first siphon and a second siphon, wherein the system is configured to prevent the first siphon from creating enough head pressure for used dialysis fluid flow from the first siphon to the second siphon until head pressure in the second siphon falls such that used dialysis fluid does not flow from the second siphon, separating used dialysis fluid flowing along the drain line to limit current flowing from the patient to a house drain.

21. The peritoneal dialysis system of claim 20, wherein the first siphon includes a first siphon tube and a first siphon chamber and the second siphon includes a second siphon tube and a second siphon chamber.

22. A peritoneal dialysis system comprising:
a cycler;
a disposable set including a patient line and a drain line, the cycler configured to pump fresh dialysis fluid to a patient via the patient line and used dialysis fluid from the patient via the drain line;
one of (i) a water purifier for supplying purified water for mixing to form fresh dialysis fluid at the disposable set, (ii) at least one fresh dialysis fluid container provided as part of the disposable set for supplying fresh dialysis fluid, or (iii) a dialysis fluid preparation unit configured to supply fresh dialysis fluid to the disposable set; and
at least one flow path insulator provided at or by at least one of the cycler, the water purifier, the dialysis fluid preparation unit, or along the drain line, the flow path insulator configured to separate used dialysis fluid flowing along the drain line, wherein the at least one flow path insulator includes a first chamber having an output directed towards but separate from a second chamber, a first valve upstream from the first chamber and a second valve upstream of the second chamber, the first and second valves sequenced to separate used dialysis fluid flowing along the drain line to limit current flowing from the patient to a house drain.

23. The peritoneal dialysis system of claim 22, wherein the first and second valves are sequenced such that used dialysis fluid flow to the first chamber is prevented if the second valve is open and the second valve is opened when the second chamber is empty.

24. A peritoneal dialysis system comprising:
a cycler;
a disposable set including a patient line and a drain line, the cycler configured to pump fresh dialysis fluid to a patient via the patient line and used dialysis fluid from the patient via the drain line;
one of (i) a water purifier for supplying purified water for mixing to form fresh dialysis fluid at the disposable set, (ii) at least one fresh dialysis fluid container provided as part of the disposable set for supplying fresh dialysis fluid, or (iii) a dialysis fluid preparation unit configured to supply fresh dialysis fluid to the disposable set; and
at least one flow path insulator provided at or by at least one of the cycler, the water purifier, the dialysis fluid preparation unit, or along the drain line, the flow path insulator configured to separate used dialysis fluid flowing along the drain line, wherein the at least one flow path insulator includes a container located upstream from a first chamber, the first chamber located upstream from a first pump, the first pump located upstream from a second chamber, the second chamber located upstream from a second pump, the first and second pumps sequenced to separate used dialysis fluid flowing along the drain line to limit current flowing from the patient to a house drain.

25. The peritoneal dialysis system of claim 24, wherein used dialysis fluid flow from the first chamber to the second chamber is prevented when used dialysis fluid flows from the second chamber.

26. A peritoneal dialysis system comprising:
a cycler;
a disposable set including a patient line and a drain line, the cycler configured to pump fresh dialysis fluid to a patient via the patient line and used dialysis fluid from the patient via the drain line;
one of (i) a water purifier for supplying purified water for mixing to form fresh dialysis fluid at the disposable set, (ii) at least one fresh dialysis fluid container provided as part of the disposable set for supplying fresh dialysis fluid, or (iii) a dialysis fluid preparation unit configured to supply fresh dialysis fluid to the disposable set; and at least one flow path insulator provided at or by at least one of the cycler, the water purifier, the dialysis fluid preparation unit, or along the drain line, the flow path insulator configured to separate used dialysis fluid flowing along the drain line, wherein the at least one flow path insulator includes a first chamber, a second chamber and a pump downstream from the first and second chambers, first and second inlet valves in fluid communication with the first and second chambers, respectively, first and second outlet valves in fluid communication with the first and second chambers, respectively, the first and second inlet and outlet valves sequenced such that used dialysis fluid flow into one of the first and second chambers occurs while used dialysis fluid is removed from the other of the first and second chambers, separating used dialysis fluid flowing along the drain line to limit current flowing from the patient to a house drain.

27. The peritoneal dialysis system of claim 26, wherein (i) in a first state the first inlet valve and the second outlet valve are open while the second inlet valve and the first outlet valve are closed and (ii) in a second state the second inlet valve and the first outlet valve are open while the first inlet valve and the second outlet valve are closed.

28. The peritoneal dialysis system of claim 26, wherein used dialysis fluid is delivered to the first and second chambers via a primary pump of the cycler.

29. A peritoneal dialysis system comprising:
a cycler;
a disposable set including a patient line and a drain line, the cycler configured to pump fresh dialysis fluid to a patient via the patient line and used dialysis fluid from the patient via the drain line;
one of (i) a water purifier for supplying purified water for mixing to form fresh dialysis fluid at the disposable set, (ii) at least one fresh dialysis fluid container provided as part of the disposable set for supplying fresh dialysis fluid, or (iii) a dialysis fluid preparation unit configured to supply fresh dialysis fluid to the disposable set; and
at least one flow path insulator provided at or by at least one of the cycler, the water purifier, the dialysis fluid preparation unit, or along the drain line, the flow path insulator configured to separate used dialysis fluid flowing along the drain line, wherein the at least one flow path insulator includes a pivoting device that pivots about a pivot, the pivoting device including first and second compartments that alternatingly fill and drain used dialysis fluid, separating the used dialysis fluid flowing along the drain line to limit current flowing from the patient to a house drain.

30. A peritoneal dialysis system comprising:
a cycler;
a disposable set including a patient line and a drain line, the cycler configured to pump fresh dialysis fluid to a patient via the patient line and used dialysis fluid from the patient via the drain line;
one of (i) a water purifier for supplying purified water for mixing to form fresh dialysis fluid at the disposable set, (ii) at least one fresh dialysis fluid container provided as part of the disposable set for supplying fresh dialysis fluid, or (iii) a dialysis fluid preparation unit configured to supply fresh dialysis fluid to the disposable set; and
at least one flow path insulator provided at or by at least one of the cycler, the water purifier, the dialysis fluid preparation unit, or along the drain line, wherein the flow path insulator includes a coiled length of tubing sized to increase a resistance to a leakage current residing in used dialysis fluid flowing through the coiled length of tubing.

31. The peritoneal dialysis system of claim 30, wherein a ratio of a length (L) of the coiled length of tubing to a cross-sectional area (A) of the coiled length of tubing is 10,000:8.

\* \* \* \* \*